United States Patent
Bertelsen et al.

(10) Patent No.: US 10,213,345 B2
(45) Date of Patent: Feb. 26, 2019

(54) APPARATUS AND PROCESS FOR PROVIDING A COILED COLLAGEN CARRIER

(71) Applicant: TAKEDA AS, Asker (NO)

(72) Inventors: Poul Bertelsen, Roskilde (DK); Henrik Neuschafer Larsen, Soborg (DK); Pernille Dybendal Pedersen, Frederiksberg (DK)

(73) Assignee: TAKEDA AS, Asker (NO)

( * ) Notice: Subject to any disclaimer, the term of this patent is extended or adjusted under 35 U.S.C. 154(b) by 911 days.

(21) Appl. No.: 14/401,702

(22) PCT Filed: May 22, 2013

(86) PCT No.: PCT/EP2013/060532
§ 371 (c)(1),
(2) Date: Nov. 17, 2014

(87) PCT Pub. No.: WO2013/174874
PCT Pub. Date: Nov. 28, 2013

(65) Prior Publication Data
US 2015/0130112 A1    May 14, 2015

(30) Foreign Application Priority Data

May 24, 2012  (DK) ................................. 2012 50178
Nov. 23, 2012  (EP) .................................... 12194089

(51) Int. Cl.
*B29C 53/32*  (2006.01)
*A61F 13/02*  (2006.01)
(Continued)

(52) U.S. Cl.
CPC ...... *A61F 13/0283* (2013.01); *A61F 13/0276* (2013.01); *A61L 24/102* (2013.01);
(Continued)

(58) Field of Classification Search
CPC .......... B29C 53/32; B29C 53/56; B29C 53/72
(Continued)

(56) References Cited

U.S. PATENT DOCUMENTS 3,759,375 A    9/1973  Nappi
4,453,939 A    6/1984  Zimmerman et al.
(Continued)

FOREIGN PATENT DOCUMENTS

CN          1580387 A  *  2/2005
DE       195 46 435 A1    6/1997
(Continued)

OTHER PUBLICATIONS

Tachosil Product Monograph Brochure, Nycomed, 2011. (Year: 2011).*

(Continued)

*Primary Examiner* — Atul P. Khare
(74) *Attorney, Agent, or Firm* — Nath, Goldberg & Meyer; Joshua B. Goldberg; Scott H. Blackman

(57) ABSTRACT

The present invention relates inter alia to an apparatus for providing a coiled collagen carrier. An apparatus according to the invention preferably comprises a device for applying moisture to a collagen carrier prior to coiling of the collagen carrier and a coiling device. The coiling device preferably comprises rotatable gripping means for gripping the collagen carrier along an edge and coiling the collagen carrier, and a support device supporting the collagen carrier while being coiled. In another aspect, the invention relates to a production facility wherein an apparatus according to invention is arranged.

20 Claims, 7 Drawing Sheets

(51) Int. Cl.
   *B29C 53/52* (2006.01)
   *B29C 53/80* (2006.01)
   *A61L 24/10* (2006.01)
(52) U.S. Cl.
   CPC .............. *B29C 53/32* (2013.01); *B29C 53/52* (2013.01); *B29C 53/8016* (2013.01); *A61L 2300/252* (2013.01); *A61L 2300/418* (2013.01); *A61L 2400/04* (2013.01)
(58) Field of Classification Search
   USPC .......................... 264/281, DIG. 40; 425/391
   See application file for complete search history.

(56) References Cited

U.S. PATENT DOCUMENTS

| | | | |
|---|---|---|---|
| 5,147,387 | A | 9/1992 | Jansen et al. |
| 5,290,310 | A | 3/1994 | Makower et al. |
| 5,334,216 | A * | 8/1994 | Vidal ................. A61B 17/0057 606/1 |
| 5,810,711 | A | 9/1998 | Scheyer |
| 5,942,278 | A | 8/1999 | Hagedorn et al. |
| 6,177,126 | B1 | 1/2001 | Hagedorn et al. |
| 7,052,713 | B2 | 5/2006 | Stimmeder |
| 8,133,500 | B2 * | 3/2012 | Ringeisen ............. A61L 27/502 424/422 |
| 9,814,686 | B2 * | 11/2017 | Schoenhofer ........ A61K 9/7007 |
| 2003/0176828 | A1 | 9/2003 | Buckman et al. |
| 2005/0155608 | A1 | 7/2005 | Pavcnik et al. |
| 2005/0178396 | A1 | 8/2005 | Hunter et al. |
| 2005/0183731 | A1 | 8/2005 | Hunter et al. |
| 2005/0186244 | A1 | 8/2005 | Hunter et al. |
| 2005/0187140 | A1 | 8/2005 | Hunter et al. |
| 2005/0196421 | A1 | 9/2005 | Hunter et al. |
| 2005/0208095 | A1 | 9/2005 | Hunter et al. |
| 2005/0214277 | A1 | 9/2005 | Schaufler |
| 2005/0234397 | A1 | 10/2005 | Poff et al. |
| 2008/0131473 | A1 | 6/2008 | Brown et al. |
| 2009/0184026 | A1 | 7/2009 | Massengale et al. |
| 2009/0275129 | A1 | 11/2009 | Cooper et al. |
| 2010/0055149 | A1 | 3/2010 | Li et al. |
| 2010/0106068 | A1 | 4/2010 | Karpiel et al. |
| 2011/0040279 | A1 | 2/2011 | Walsh |
| 2011/0140316 | A1 | 6/2011 | Bagga et al. |
| 2012/0052040 | A1 | 3/2012 | Hunter et al. |
| 2012/0207808 | A1 | 8/2012 | Evans et al. |
| 2014/0072612 | A1 | 3/2014 | Schoenhofer et al. |

FOREIGN PATENT DOCUMENTS

| | | | |
|---|---|---|---|
| DE | 19546435 A1 | 6/1997 | |
| DE | 202006009712 U1 | 10/2007 | |
| EA | 006686 B1 | 2/2006 | |
| EP | 1053757 A1 | 11/2000 | |
| EP | 2052746 A2 | 4/2009 | |
| EP | 2163230 A1 | 3/2010 | |
| GB | 422990 | 1/1935 | |
| GB | 423017 | 1/1935 | |
| GB | 487258 | 6/1938 | |
| GB | 1406015 A * | 9/1975 | ......... A22C 13/0003 |
| JP | 2004-73221 A | 3/2004 | |
| JP | 2004-188037 A | 7/2004 | |
| JP | 2004-520124 A | 7/2004 | |
| JP | 2005-506110 A | 3/2005 | |
| JP | 2007-159866 A | 6/2007 | |
| JP | 2010-12127 | 1/2010 | |
| JP | 2014-519897 A | 8/2014 | |
| RU | 2018540 C1 | 8/1994 | |
| RU | 2118176 C1 | 8/1998 | |
| RU | 2188206 C2 | 8/2002 | |
| RU | 2235539 C1 | 9/2004 | |
| WO | 94/13210 A1 | 6/1994 | |
| WO | 9721383 A1 | 6/1997 | |
| WO | 02/058750 A2 | 8/2002 | |
| WO | 02058749 A2 | 8/2002 | |
| WO | 02/070594 A2 | 9/2002 | |
| WO | 03009764 A1 | 2/2003 | |
| WO | 2006/044879 A2 | 4/2006 | |
| WO | 2006/044882 A2 | 4/2006 | |
| WO | 2006/119256 A2 | 11/2006 | |
| WO | 2007/117855 A1 | 10/2007 | |
| WO | 2009/109963 A1 | 9/2009 | |
| WO | 2009/126870 A2 | 10/2009 | |
| WO | 2009/134447 A1 | 11/2009 | |
| WO | 2012159635 A1 | 11/2012 | |

OTHER PUBLICATIONS

Carbon, RT et al., "Tissue Sealing Concept in Minimally Invasive Surgery in Children", Pediatric Endosurgery & Innovative Techniques, vol. 5, Issue 1, pp. 5-12, (Jul. 8, 2004).
Carbon, RT et al. "Innovative tissue management in MIS", Minimally Invasive Therapy & Allied Technologies, vol. 8, Issue 5, pp. 347-353, (Jul. 10, 2009).
Saif, R et al., "Use of Fibrin-Based Sealants and Gelatin-Matrix Hemostats in Laparoscopic Liver Surgery", Surgical Laparoscopy, Endoscopy & Percutaneous Techniques, vol. 21, Issue 3, pp. 131-141 (Jun. 2011).
Lee, MGM et al. "Application of Fibrin Sealant in Surgery", Surgical Innovation, vol. 12, No. 3, pp. 203-213 (2005).
Somil R et al. "Newer Haemostats in Cannine Practice", International Journal of Agricultural Sciences and Veterinary Medicine, vol. 1, No. 3, pp. 88-94 (Aug. 2013).
Wheat, JC et al. "Advances in Bioadhesives, Tissue Sealants, and Heostatic Agents", Urologic Clinics of North America, Elsevier (2009).
de Cogain, MR et al. "Advances in Tubeless Percutaneous Nephrolithotomy and Patient Selection: An Update", Current Urology Reports, Springer Link, vol. 14, Issue 2, pp. 130-137 (Apr. 2013).
Lewis, KM et al. "Control of bleeding in surgical procedures: critical appraisal of HEMOPATCH (Sealing Hemostat)", Medical Devices: Evidence and Research, Dove Press, issue 9, pp. 1-10, (2016).
Liu T et al. "Comparison of the Nuss and sternal turnover procedures for primary repair of pectus excavatum" Asian Journal of Surgery, vol. 37, pp. 30-34 (2014).
Singh I "Robot-assisted laparoscopic partial nephrectomy: Current review of the technique and literature", Journal of Minimal Access Surgery, vol. 5(4), pp. 87-92 (Oct.-Dec. 2009).
2016 Iran Search Results from counter-part Iran No. 13915014000301810.
2016 Photograph of Endodock® apparatus in retracted configeration.
2016 Photograph of Endodock® apparatus in extended configuration.
2016 Endodock® Instruction Leaflet by Nycomed.
Fukui,Atsushi ;Aomori Rinsanpu Shi;Journal of Aomori Society Obstetricians ;year 2007; vol. 22 ;No. 1; pp. 20-25; "A case of laaroscopically detected severe adhesion and diastasis caused by the fibrinogen sheet placed at adenomyomectomy" (including partial translation).
Screenshot of www.tachosil.com; 2014; Takeda.
Bisertes, Jacques. "TachoSil: the value of its use in urologic surgerys" Journal De Chirurgie, Paris 2007 vol. 144(1), pp. 82-83.
Lattouf et al. "Practical hints for hemostasis in laparoscopic surgery", Minimally Invasive Therapy, 2007, 16(1), pp. 45-51.
Liatsikos et al. "Cautery Free Nerve Sparing Extraperitoneal Endoscopic Radical Prostatecomy: The Use of TachoSil for Hemostasis". Journal of Endourology. 2006, 20(1), A294.
Murphy et al. "TachoSil is an Effective Haemostatic Aid During Laparoscopic Partial Nephrectomy in a Porcine Model". European Urology Supplements. 2006, 5(2), p. 329.
Nohuz, Erdogan, et al., "Efficiency of TachoSil to Prevent Postsurgical Adhesion Development on Laparoscopic Rat Model", Gynecol Surg, vol. 6, 2009, pp. 323-329.
Rane et al. "Evaluation of a Hemostatic Sponge (TachoSil) for Sealing of the Renal Collecting System in a Porcine Laparoscopic Partial Nephrectomy Survival Model". Journal of Endourology, 24(4), 2010.

(56) References Cited

OTHER PUBLICATIONS

Ahmed et al. BJUI Letters. Journal Compilation, 2009, 104, 269-272.
Carbon et al. "Minimalinvasive Kinderchirurgie: Entwicklung und Fortschritt durch innovative Technologie". Kiln Padiatr. 2001. 213, pp. 99-103.
Carbon et al. "Fast-track Surgery of Recurrent Pneumothorax in Patients with Cystic Fibrosis—Superiority of Minimally Invasive Tissue Management (ATSS)". Medimond, 2007, pp. 15-28.
Carbon et al. "AMISA: innovative tissue management in MIS". Minimally Invasive Therapy & Allied Technologies. 1999, 8(5) 347-353.
Erdogru et al. "Laparoscopic transvesical repair of recurrent vesicovaginal fistula using with fleece-bound sealing system". Archives of Gynecology and Obstetrics. 2008, 277, pp. 461-464.
Gordon, L.E., "The New Science of Strong Materials or Why You Don't Fall Through the Floor", 1976, pp. 38-43.
TachoSil. A guided tour. Brochure, 2007.
Nakajima et al. "A Simple Application Technique of Fibrin-Coated Collagen Fleece (TachoComb) in Laparoscopic Surgery". Surgery Today. 2007, 37, pp. 176-179.
Rickenbacher et al. "Efficacy of TachoSil a fibrin-based haemostat in different fields of surgery—a systemic review". Expert Opinion on Biological Therapy. 2009, 9(7), pp. 897-907.
Sanseverino et al. "Laparoscopic Partial Nephrectomy with Parenchimal Haemostasis with TachoSil Application". Journal of Endourology. 2009, 23, p. A362.
Slupski et al. Suture-Free Laparoscopic Partial Nephrectomy—Improvement of Hemostasis with Human Fibrinogen and Thrombin-Coated Collagen Patch (TachoSil). European Urology Supplements. 2010, 9(6), p. 636.
van Dijk et al. "Haemostasis in laparoscopic partial nephrectomy: Current status". Minimally Invasive Therapy & Allied Technologies. 2007, 16(1), pp. 31-44.
Simo, et al., "Hemostatic Agents in Hepatobiliary and Pancreas Surgery: A Review of the Literature and Critical Evaluation of a Novel Carrier-Bound Fibrin Sealant (TachoSil)", ISRN Surgery, vol. 2012, 12 pages.
"Highlights of Prescribing Information", TachoSil (Absorbable Fibrin Sealant Patch), Initial U.S. Approval, 2010, twelve pages.
Russian office action dated Feb. 2, 2017 for corresponding Russian Patent Application No. 2014907745 with English translation attached.
Brochuere, Wissenwertes ueber Tachosil für Operateure, Nycomed 2009.
Carbon et al. "Innovatives Gewebemanagement in der minimal invasiven Chirurgie". Medizin & Wissen, 2000. English Translation attached.

\* cited by examiner

APPARATUS AND PROCESS FOR PROVIDING A COILED COLLAGEN CARRIER

This application is filed under 35 U.S.C. 371 as the US national stage of PCT/EP2013/060532, filed May 22, 2013, which claims priority to PCT/DK2012/050178, filed May 24, 2012 and EP 12194089.4, filed Nov. 23, 2012.

TECHNICAL FIELD OF THE INVENTION

The present invention relates inter alia to an apparatus for providing a coiled collagen carrier. An apparatus according to the invention preferably comprises a device for applying moisture to a collagen carrier prior to coiling of the collagen carrier and a coiling device. The coiling device preferably comprises rotatable gripping means for gripping the collagen carrier along an edge and coiling the collagen carrier, and a support device supporting the collagen carrier while being coiled. In another aspect, the invention relates to a production facility wherein an apparatus according to invention is arranged. In a further aspect, the invention relates to a process for coiling a collagen carrier. The collagen carrier preferably comprises (i) a collagen layer and (ii) a coating layer comprising fibrinogen and thrombin, and the process comprises the sequential steps of humidifying at least part of said collagen carrier, coiling said collagen carrier drying the coiled collagen carrier, so as to provide a form-stable coiled collagen carrier The present invention also relates to a process for the preparation of a rolled collagen carrier, or a compressed collagen carrier or a rolled compressed collagen carrier.

In addition, the present invention relates to a rolled compressed collagen carrier, said rolled compressed collagen carrier being obtainable by said process.

BACKGROUND OF THE INVENTION

Medicated sponges are used during open surgery to stop local bleeding (hemostasis/haemostasis). They react upon contact with blood, other body fluids or saline to form a clot that glues the sponge to the tissue surface and hemostasis is reached in a few minutes. Medicated sponges are sponges, such as a collagen carrier as defined below, such as a cellulose sponge as disclosed in EP2052746.

Collagen has been used as a haemostatic agent for decades. A product that combines the haemostatic features of fibrin glue with the asset of collagen as a carrier has been developed and manufactured under the trademark Tacho-Sil®. TachoSil® is a ready-to-use collagen carrier with a coating of the active components of fibrin glue: human fibrinogen and human thrombin. The product is described in WO 02/058 749, WO 02/070 594 and WO 02/058 750.

TachoSil® contains fibrinogen and thrombin as a dried coating on the surface of a collagen sponge. In contact with body fluids, e.g. blood, lymph or physiological saline solution the components of the coating dissolve and partly diffuse into the wound surface. This is followed by the fibrinogen-thrombin reaction which initiates the last phase of physiological blood coagulation. Fibrinogen is converted into fibrin monomers which spontaneously polymerise to a fibrin clot, which holds the collagen sponge tightly to the wound surface.

TachoSil® has been sold since 2004 by Nycomed and is used in open surgery for hemostasis and sealing. Traditionally open surgery usually requires a long incision of the skin.

Contrary to open surgery, a minimally invasive procedure is any procedure (surgical or otherwise) that is less invasive than open surgery used for the same purpose. Minimally invasive surgery (MIS) procedures are performed through one or more access orifices e.g. short incisions ('keyhole surgery') or through natural body openings. Hence, MIS procedures require specially designed surgical instruments which are placed through these access orifices. In abdominal surgery, the access of the instruments is usually done through so-called trocars, which are mostly rigid tubes with a typical inner diameter of 5 to 12 mm. The small size of the access orifices used in MIS restricts what can be inserted into the orifices. Therefore, all surgical tools and materials used in MIS procedures must be of a size and condition that allow for their insertion through the access orifices and they need, of course, as all medical tools to be sterile. Hence, tools and materials are most often specially designed for use in MIS.

WO 97/21383 (Nycomed Arzneimittel GmbH) discloses a surgical instrument comprising an applicating member, wherein the applicating member comprises a rodshaped portion so as to allow a sheet of surgical material such as, e.g. TachoComb® (coated equine collagen sponge/Nycomed) to be rolled up to form a carpetlike roll of surgical material on the rod-shaped portion of the applicating member. However, this manual instrument for hand-rolling surgical materials, such as collagen carriers, has several disadvantages as described below. WO 02/058749 discloses the non-sterile insertion of TachoComb® into an endoscopic equipment, wherein the sample is flattened manually to be able to wrap it manually around a guiding "pin". WO 02/058749 teaches that the collagen product "has to stay flexible enough in dry condition to be bent and rolled up" (p 29, lines 19-20). Thus WO 02/058749 only relates to manual (i.e. hand-rolled), non-sterile rolling of TachoComb® and further teaches that the rolling process must be "dry". One significant problem with the above methods which use an applicating member or guiding pin for hand-coiling the collagen carrier arises in case application of multiple rolled/coiled collagen carriers is necessary in quick succession (e.g. either because one collagen carrier is insufficient to completely stop the bleeding, or due to an error in application of the first collagen carrier(s)). In this instance the same applicating member cannot be used to apply the second collagen carrier: instead, multiple applicating members must be prepared. This is because in order to apply collagen-based products such as the TachoComb® product correctly, the applicating member must be completely dry in order to avoid activating the adhesive properties of the collagen carrier. If the collagen carrier becomes prematurely wet by contacting a wet application member or guiding pin, the carrier will stick to the applicating member/guiding pin and/or become an unusable sticky lump of material. Another way of rolling up collagen-based surgical sheets is for the surgeon to use his/her hands in the same way as for rolling up a cigarette, however for this and all the manually-rolled cases above the rolled surgical product is not form-stable and is therefore more difficult to manipulate in a controlled manner after insertion into the body: the non-form-stable product may "spring open" in an uncontrolled way during the unrolling process and adhere incorrectly. This is a particular issue for MIS surgery, where it is harder to manipulate the product once it is in the body as one only has indirect access to the surgical sheet via endoscopic surgical instruments. One way of lessening the effect of the rolled collagen-based surgical product being non-form-stable is to tie the rolled product together with a suture, however this solution is only relevant where the coiled carrier in not unrolled in vivo but rather maintained in the patient in a coiled state (e.g. in a partial nephrectomy procedure).

For applications such as MIS there is thus a need to produce an improved coiled collagen-based surgical product, which has dimensions useful for MIS applications and useful properties for promoting coagulation and wound sealing, but which allows easy application of more than one collagen carrier in quick succession and furthermore gives the surgeon improved control of the complex process of moving the carrier to the desired tissue site and applying it.

A further problem with all the above types of manual coiling processes for collagen carriers is that the results are of course highly dependent on the skills of the individual medical practitioner carrying out the coiling process, and therefore highly variable in reproducibility, and may lead to a non-sterile product, un-even and thus un-reproducible coiling/rolling of the collagen carrier, and un-predictable loss of coating.

Thus, there exists a need in the art for a collagen carrier coated with human fibrinogen and human thrombin especially designed for use in minimally invasive surgery that is ready-to-use, maintains sterility, and which has an acceptable hemostatic and tissue sealing effectiveness and adhesive strength to living tissue, and also which allows easy application of more than one collagen carrier in quick succession for MIS techniques, and also allows the surgeon more control on application to the desired tissue during an MIS procedure in order to avoid adhesion of the collagen carrier to an incorrect site, would be advantageous.

Hence, a ready-to-use collagen carrier coated with human fibrinogen and human thrombin designed particularly for use in MIS, such as designed to fit an access tube and/or orifice in MIS, preferably such as to be inserted into endoscopic devices would be advantageous, and in particular a ready-to-use collagen carrier coated with human fibrinogen and human thrombin having an acceptable hemostatic effectiveness, adhesive strength to living tissue and sterility that is ready-to-use in MIS, allows easy application of more than one collagen carrier in quick succession for MIS techniques, and also allows the surgeon more control on application to the desired tissue during an MIS procedure in order to avoid adhesion of the collagen carrier at the incorrect site, would be advantageous.

SUMMARY OF THE INVENTION

It is an object of the present invention to provide an apparatus and process capable of providing a ready-to-use collagen carrier coated with human fibrinogen and human thrombin designed e.g. for use in minimally invasive surgery, such as designed preferably to be inserted into endoscopic devices.

Thus, in a first aspect the present invention relates to an apparatus for providing a coiled collagen carrier. The apparatus comprises preferably
  a device for applying moisture to a collagen carrier prior to coiling of the collagen carrier,
  a coiling device comprising
    rotatable gripping means for gripping the collagen carrier along an edge and coiling the collagen carrier, and
    a support device supporting the collagen carrier while being coiled.

In preferred embodiments, the invention relates an apparatus for providing a coiled collagen carrier, the apparatus comprising a device for applying moisture to a collagen carrier prior to coiling of the collagen carrier,
  a coiling device comprising
    rotatable gripping means for gripping the collagen carrier along an edge and coiling the collagen carrier, and
    a support device for supporting the collagen carrier while being coiled.

Preferably, the gripping device comprises a pair of elongated members, such as a pair of tweezers or pincers.

The support device may in some preferred embodiments also serve a storage purpose in the sense that the coiled collagen carrier may be stored and protected from mechanical influence in the support device prior to any further handling of the coiled collagen carrier. A lid may be applied to the support device during storage to protect and prevent the coiled collagen carrier from falling out of the support device. Such lids are installed e.g. after the coiled collagen carriers have been dried in e.g. a drying tunnel.

The support device may preferably be or comprise a cavity having a bottom shaped as a segment of a cylinder and having at least one open end. The curved part of the cylinder segment extends preferably at least 180°, such as extends 180°. In addition, the cavity may preferably be channel-formed with two parallel side wall extending from the bottom.

Such a channel-shaped cavity may preferably have a generally "U"-shaped cross section, wherein the bottom of the cavity forms the curved part of the "U"-shaped cross-section and each side wall forming the straight parts of the "U"-shaped cross section.

An apparatus according to the present invention may preferably be adapted to move the pair of elongated member in reciprocating movement, so that the elongated members can be retracted after the collagen carrier has been coiled. The reciprocating movement is typically in a direction being aligned with an longitudinal extension of the elongated members.

Preferred embodiments of the apparatus may further comprise a compressing device arranged to compress the moisturised collagen carrier prior to coiling of the moisturised collagen carrier. The compressing device may preferably comprise a pair of rollers arranged to compress the moisturised collagen carrier prior to coiling of the moisturised collagen carrier.

Preferred embodiments of the apparatus may further comprise at least a drying means for drying one or more coiled collagen carriers subsequently to the coiling. The means for drying is preferably designed to dry off the moisture applied to the collagen carrier prior to coiling. The at least one drying means may preferably comprise a drying tunnel through which the coiled collaged carriers are conveyed while being present in the support device.

The drying means may preferably comprise a pump sucking or blowing air, preferably being sterile filtered. The air pumped or sucked is preferably sucked or pumped through the drying tunnel and the temperature of the air may preferably be higher than the temperature of the coiled collagen carrier. In addition, means for applying heat inside the drying tunnel may preferably be applied. In some preferred embodiments, the air sucked or blown is air from the surroundings of the apparatus, which often means that the air used is the air present in the room where the apparatus for coiling a collagen carrier is located and that air is used without any pre-conditioning such as heating, cooling, sterilization etc.

The direction of the air being sucked or blown though the drying tunnel may preferably be counter current to the conveying direction of the coiled collagen carriers or is in the same direction as the conveying direction of the coiled collagen carriers. In some preferred embodiments, the air being sucked or blown is sucked and blown in both directions. In the latter case, the suction or blowing is done through a opening arranged midway downstream of the drying tunnel and the air escaping (when blowing) or entering (when sucking) through the opens ends of the drying tunnel.

Preferred embodiments of the apparatus according to the invention may preferably comprise a first conveyer device which conveys collagen carriers prior to coiling past the moisturiser device and to the coiling device.

Preferred embodiments of the apparatus according to the invention may preferably comprises a guide means for guiding and conveying the collagen carrier from the device for applying moisture, through a compressing device (if present) and to a coiling device. By guiding is preferably meant that the path the collagen carrier can follow is spatially restricted by the conveyer means of the guiding means.

In embodiments comprising a pair of rollers arranged to compress the moisturised collagen carrier prior to coiling of the moisturised collagen carrier, the first conveyer device conveys the moisturised collagen carriers to the pair of rollers. In general, the first conveyer device may convey the moisturised collagen carrier to the compressing device.

The first conveyer device may preferably comprise two conveying elements, preferably in the form of two separate conveyer belts. One element is adapted to convey the collagen carrier towards the moisturiser device and a second conveying element for conveying the collagen carrier past the moisturiser device and towards the pair of rollers or compression device.

Guide means may be present for guiding the humidified collagen carrier through a compression device, if present, and to the coiling device.

The cavity of the supporting device may preferably be formed in a second conveyer device of the apparatus. Alternatively or in combination thereto, the cavity of the supporting device may be formed in a tray having a plurality of cavities, said tray being arranged on and conveyed by a second conveyer device of the apparatus.

According to preferred embodiments of the invention, the apparatus may preferably comprise a cabinet sealing the moisturiser device, and/or the rollers, and/or the coiling device, and/or the support device, and/or the first and/or the second conveyer device. By sealing is preferably meant that the cabinet prevents some moisture from leaking to the surrounding of the apparatus. In addition or alternatively thereto, the apparatus may further comprise suction means for sucking out gas and/or droplets originating from the humidification. This preferably includes that a chamber in which the collagen carrier is humidified and coiled as well as the drying tunnel comprises openings allowing air to be sucked in or blown out.

Preferred embodiments of the apparatus may further comprise a device for conveying a coiled collagen carrier from the supporting device and arranging it in an inner container. Such a device may be a numerically controlled robot.

To close the inner container, the apparatus may further comprise a cover arranging device arranging a cover to at least the opening of the inner container.

In some preferred embodiments, the cover is heat welded or glued to the inner container and the apparatus may further comprise a heat welding device or a gluing device heat welding or gluing the cover to the inner container.

The cover is preferably gas and/or liquid permeable and the inner container with the cover forms a closed inner container to be arranged in a outer container. Preferred embodiments of the apparatus may further comprise a device arranging the inner container in an outer container.

In some preferred embodiments, the outer container is closed by heat welding or gluing and the apparatus may further comprise a heat welding device or a gluing device closing the outer container by heat welding or gluing.

The apparatus may further comprise a device for arranging a desiccant inside the outer container and outside the inner container for providing a packed coiled collagen carrier; e.g. a coiled collagen carrier arranged inside an inner container with cover which together with a desiccant is arranged inside and outer container.

The device(s) for conveying and/or arranging the coiled collagen carrier, the cover, the desiccant and/or the inner container may preferably be a numerically controlled robot arm with gripping means.

Preferably, the apparatus may comprise a sterilizing device arranged to sterilize the packed coiled collagen carrier. The apparatus may further comprise sterilizing devices for sterilizing the collagen carrier at other steps of the production, e.g. for sterilizing the coiled collagen carrier when arranger in the inner container with cover. Preferably, the sterilizing device comprises a source of radio magnetic radiation. Alternatively, the sterilizing may be performed remote from the apparatus, e.g. by shipping the collagen carriers either being packed or not packed to a sterilization department remote from the production site for coiled collagen carriers.

An apparatus according to the present invention, may further comprise one or more image recognition devices adapted to image the processing of the apparatus at preselected stages, examine the images and signal a discard signal for a coiled collagen carrier in case the examining reveals that a coiled collagen carrier falls outside quality ranges.

An apparatus according to the present invention may further comprise one or more air-conditioning devices maintaining the atmosphere surrounding the collagen carrier and humidification device while being humidified compressed and coiled at a temperature of 18-22° C. and a relative humidity of 30-50%.

In a second aspect the invention relates to a production facility wherein different elements or parts of an apparatus according to the present invention are spatially distributed in a preferred manner.

Preferably, the elements or parts of an apparatus according to the present invention providing the coiled collagen carrier arranged in an inner container with cover applied may be arranged in a primary production room being sealed by airlocks.

In combination thereto, the elements or part of an apparatus according to the present invention packaging the inner container in a outer container with a desiccant may preferably be arranged in a secondary production room sealed by airlocks. Preferably, the primary and secondary production rooms are connected by a conveyer extending in between the two production rooms and comprising an airlock; the inner container being conveyed by the conveyer from the primary production room to the secondary production room.

In a third aspect, the invention relates to a process for coiling a coated carrier, the process utilises preferably an apparatus according to any of the preceding claims and the coated carrier comprising (i) a carrier layer and (ii) a coating layer comprising fibrinogen and thrombin, said process comprising the sequential steps of:

humidifying at least part of said coated carrier,
coiling said carrier
drying the coiled coated carrier,
so as to provide a form-stable coiled collagen carrier The carrier may preferably comprise one or more of collagen, cellulose, oxidised regenerated cellulose, a woven mesh of oxidized, regenerated cellulose with polyglactin 910 filaments. Furthermore, the characteristics of the carrier presented herein may constitute or at least form part of the carrier. The coated carrier is preferably a collagen carrier as disclosed herein.

Drying is preferably considered to have been completed when the residual amount of the liquid used for humidifying (or other liquid substances) is lower than a pre-selected limit (please see below for preferred and acceptable residual amounts). It is noted that in many of the preferred embodiments, the drying requirement is implemented as a drying time to avoid time-consuming and/or destructive measurements of the actual value for the residual amount in coiled collagen carrier produced according to the present invention.

In preferred embodiments of the process, at least the coating layer of said collagen carrier is humidified. Preferably, the coating layer has been humidified using a solvent. Thereby the coating is softened. The collagen carrier is often flexible and there is therefore often no need to soften the collagen part of the collagen carrier.

Preferably the collagen carrier is humidified on the coating layer by a solvent in an amount 1.2-10.75 mg/cm$^2$ surface of the coating layer. Preferably, the solvent comprises or consists of ethanol. Water is generally not preferred as solvent. Furthermore, as the collagen carrier not including the coating layer typically is soft it if often not necessary or desired to humidify the collagen part of the collagen carrier.

In a process according to the present invention, the collagen carrier may be compressed subsequently to humidifying and prior to coiling with a compression ratio between 6-12. The compression ratio is typically and preferably considered to be the ratio between the thickness of the collagen carrier before and after compression. It is noted, that the collagen carrier after it has been compressed may experience some relaxation resulting in that the compressed collaged carrier may revert towards its state before being compressed if left at rest with no further subsequent processing due to the flexible nature of the collagen carrier. In such cases, the thickness after compression is considered to be either the thickness of the collagen carrier while being compressed, which often resembles the distance between the elements performing the compression (such as the gap size between a pair of rollers), or the thickness of the compressed collagen carrier immediately after it has been compressed.

A process according to the present invention may further comprise the step of arranging the form-stable coiled collagen carrier in an inner container. Preferably, the process may subsequently comprise the step of closing the inner container by applying a cover to the inner container. Further, a process according to the present invention may comprise a further subsequent step of arranging the inner container in an outer container, and sealing the outer container. In combination thereto, a process according to the present invention may comprise the step of arranging a desiccant inside the outer container and outside the inner container.

The arrangement of the form-stable coiled collagen carrier in the inner container and closing inner container may preferably be performed in a primary production room and the arrangement of the inner container in an outer container is performed in a secondary production room. The first and the secondary production rooms may be connected with each other by an airlock and the closed inner container is transported from the first to the second room via the airlock.

Further, a process according to the present invention may comprise arranging a desiccator inside the outer container prior to sealing of the container.

Preferred embodiments of the process according to the present invention may further comprise the step of sterilizing the coiled collagen carrier. The sterilizing step may preferably be carried out when the inner container with cover is arranged inside the outer container together with a desiccant and after the outer container has been closed.

A process according to the present invention is preferably is carried out as an assembly-line process in which the collagen carrier is conveyed without intermediate storing between humidifying preferably only by ethanol and coiling and between coiling and drying off preferably only ethanol.

The humidifying of the collagen carrier may preferably be performed when a humidified collagen carrier may proceed directly to coiling without any intermediate storing.

Definitions

Prior to discussing the present invention in further details, the following terms and conventions will first be defined:

The term "collagen carrier" is in the present context any suitable carrier comprising collagen that can have a coating layer that comprises/consist of a collagen layer and/or a coating layer. The collagen carrier can in one embodiment be rolled or coiled (the words "rolled" and "coiled" are used interchangeably herein). The coiled collagen carrier of the present invention can in one embodiment be a compressed, coiled collagen carrier, or in another embodiment an unrolled version of a compressed, coiled collagen carrier. Preferably, the collagen carrier is a collagen sponge comprising or consisting essentially of collagen type I fibres and a coating. Although the carrier material is preferably a collagen sponge which comprises collagen type I material from mammalian, transgenic or recombinant sources, it can also comprise another type of collagen, for example one or more of collagen type I, II, III, IV, VII and/or X. Preferably the collagen carrier, such as a collagen sponge, is coated with the human coagulation factors fibrinogen and thrombin and optionally also riboflavin (a yellow colouring agent used to aid in identifying the active side of the collagen carrier). Thus in one embodiment of the present invention, the collagen carrier is a collagen sponge consisting essentially of collagen type I fibres and a coating of fibrinogen, thrombin and riboflavin. Fibrinogen and thrombin can for example be human fibrinogen and thrombin, and can be purified from a natural source, or can alternatively be e.g. transgenic or recombinant human fibrinogen and thrombin, or can be manufactured by other methods such as e.g. chemical synthesis. Fibrinogen and thrombin are preferably solid or mostly solid and in one embodiment can be human of origin. In another embodiment, at least one and more preferably both of the components fibrinogen and thrombin have the human amino acid sequence and can be produced by recombinant technology, inclusion bodies or chemical synthesis. The thrombin and fibrinogen are in one embodiment dry, such as containing less than 5% water, such as less than 4% water, such as less than 3% water, such as less than 2% water, such as less than 1% water, such as less than 0.8% water, such as less than 0.6% water, such as less than 0.4% water, such as less than 0.2% water, such as less than 0.1% water.

In one embodiment of the present invention, the collagen carrier comprises or consists of (i) a collagen layer and (ii) a coating layer comprising fibrinogen and optionally thrombin and optionally a colouring agent such as e.g. riboflavin. The collagen carrier may in an embodiment further comprise other peptides, such as other peptides capable of causing haemostasis.

In one embodiment of the present invention, the expressions collagen sponge, collagen fleece, collagen patch or simply fleece or patch are terms that are used synonymously to mean a collagen carrier. A carrier may alternatively to collagen comprise a biodegradable co-polymer or a polymer such as a polyhyaluronic acid, polyhydroxy acid, e. g. lactic acid, glucolic acid, hydroxybutanoic acid, a cellulose, or gelatine. Another alternative carrier may be polyglactin 910, i.e. a synthetic, absorbable copolymer of 90% glycolide ($C_2H_2O_2$) and 10% lactide ($C_6H_8O_4$); such as e.g. with molecular formula $(C_2H_2O_2)_m$ and $(C_3H_4O_2)_n$. A further alternative carrier may be equine collagen, such as e.g. native equine collagen extracted from sinews or tendons.

Thus, the collagen part of the collagen carrier can in one embodiment of the present invention be substituted with a non-collagen matrix that is coated in the same way as for the collagen carrier as described herein, i.e. in one embodiment of the present invention is provided a carrier comprising or consisting of a non-collagen matrix coated with a coating comprising or consisting of fibrinogen and thrombin. One example of a suitable non-collagen matrix is a cellulose fabric. In one embodiment of the present invention, the non-collagen matrix is an oxidized regenerated cellulose fabric sheet attached to a non-woven polyglactin 910 felt.

However, it is preferably a collagen carrier preferably having a shape suitable for a medicated sponge. In an embodiment of the invention, the collagen carrier which is to undergo the coiling process of the present invention is identical to Tachosil® or TachoComb® available from Nycomed, such as described in WO 02/058 749, WO 02/070 594 and WO 02/058 750.

A preferred collagen layer is preferably used to mean a collagen sponge produced by the method according to the invention as disclosed in WO 02/070594. The collagen layer used in the present invention preferably fulfills at least one, such as at least two or at least three, of the following criteria:
pH-value between 5.0 and 6.0,
lactic acid content at the most 5%,
ammonium content at the most 0.5%,
soluble protein content, calculated as albumin content, at the most 0.5%,
sulphate ashes content at the most 1.0%,
heavy metal content at the most 20 ppm,
microbiological purity, at the most 103 CFU/g,
collagen content of 75% to 100%,
density of 1-10 mg/cm$^3$, such as 2-7 mg/cm$^3$,
elasticity module of 5-100 N/cm$^2$, such as 10-50 N/cm$^2$, and wherein when isolating parts of the sponge, the sponge will have the following properties:
elasticity module in the range of 5 to 100 N/cm$^2$,
density in the range of 1 to 10 mg/cm$^3$,
chamber diameter of more than 0.75 mm and less than 4 mm, or a chamber diameter average of at most 3 mm.

Please note that the density of a collagen carrier is the density of the collagen carrier excluding the coating layer.

Preferably the collagen layer fulfills at least the following:
pH-value between 5.0 and 6.0,
lactic acid content at the most 5%,
ammonium content at the most 0.5%,
soluble protein content, calculated as albumin content, at the most 0.5%,
sulphate ashes content at the most 1.0%,
heavy metal content at the most 20 ppm,
microbiological purity, at the most 103 CFU/g,
collagen content of 75% to 100%,
density of 1-10 mg/cm$^3$, such as 2-7 mg/cm$^3$.

Further, the collagen layer is air and liquid tight in the sense that, once the collagen sponge is applied to a wound, it will not allow air or liquid to pass through the collagen layer. Liquids are absorbed in the layer. This effect is primarily achieved due to the fact the collagen layer has a three-dimensional structure with stacked chambers separated and substantially totally enclosed by walls of collagen material, in contradiction to known collagen sponges which have a fibre structure.

In the present context, the term "chamber diameter" should be understood as the largest straight-line wall-to-wall distance in a chamber, i. e. as the largest diagonal straight-line distance of a chamber. The chambers may be of a polygonal shape, such as of an octagonal shape. Thus, when the carrier is cut, the chambers are divided and cut to caverns.

It has been found that a chamber diameter of more than 0.75 mm and less than 4 mm, or a chamber diameter average of at most 3 mm, renders the collagen sponge particularly useful for being coated with a fibrin glue preparation. When the carrier is cut, the chambers are divided and cut to caverns. The preferably solid fibrinogen and the preferably solid thrombin is fixed to the collagen layer and most of it is present in the caverns thus providing a substantially even distribution of the preferably solid thrombin and preferably solid fibrinogen. Due to this and the fixation, it is possible to introduce substantial amounts of fibrinogen and thrombin on the carrier in contrast to the situation where liquid compositions of thrombin and fibrinogen are e. g. dropped or sprayed onto the material.

Each coated collagen carrier as well as the uncoated collagen layer is inspected visually for the "pore size distribution"—no pores wider than 4 mm and deeper than 2 mm are allowed. These sizes are measured with a ruler if necessary.

By fixation of the coating layer to the collagen layer is preferably meant that the coating layer adheres through mechanical interactions i.e. by inclusion onto the collagen carrier pore surface and within the coating layer.

In a preferred embodiment of the present invention, the amount of fibrinogen and thrombin/cm$^2$ in the coating layer can be:
Thrombin 1.3-2.7 IU/cm$^2$ and/or
Fibrinogen 3.6-7.4 mg/cm$^2$ In an embodiment, the above mentioned amounts of fibrinogen and thrombin/cm$^2$ are identical to Tachosil® or TachoComb® available from Nycomed, such as described in WO 02/058 749, WO 02/070 594 and WO 02/058 750.

By substantially even distribution of the solid thrombin and solid fibrinogen is meant that the coating layer is substantially evenly distributed across the collagen layer meaning that local changes in thickness of the coating layer is observed visually by SEM cross sections i.e. the coating layer may be located on the surface and sometimes at a lower level in an open cell. There should not be any through-going cracks (fissures) on the coating layer.

In an embodiment a collagen carrier according to the present invention may have a size of 92-98 mm*46-50 mm*4-7 mm and this carrier is called a large size collagen carrier and has the shape of a box of rectangular cross-section with all sides flat. Hence, the area of the largest rectangular cross-section is about 42.3-49.0 cm². In another embodiment a midi size collagen carrier according to the present invention is 46-49 mm*46-50 mm*4-7 mm, and has the shape of a square box of quadrant cross-section. Hence, the area of the quadrant cross-section is about 21.2-24.5 cm². A midi size collagen carrier according to the invention is preferred. In yet another embodiment a mini size collagen carrier according to the invention is 28-33 mm*23-27 mm*4-7 mm, and has the shape of a box of rectangular cross-section with all sides flat. Hence, the area of the largest rectangular cross-section is about 6.4-8.9 cm².

In an embodiment of the invention, a collagen carrier has at least one of the following physical properties, such as at least two of the following physical properties, such as at least three of the following physical properties, such as at least four of the following physical properties: elasticity module in the range of 5-100 N/cm², density of 1-10 mg/cm³, chamber diameter of more than 0.75 mm and less than 4 mm and/or having a chamber diameter average below 3 mm and evenly distributed and fixed upon said collagen carrier solid fibrinogen and solid thrombin. Please note that the density of a collagen carrier is the density of the collagen carrier excluding the coating layer.

"Mechanically stable" is meant to refer to "form-stable".

Form-stable as used in form-stable coiled collagen carrier is preferably used to mean a coiled collagen carrier which maintains its geometrical shape without being fixated by constraining or constriction elements not forming part of the collagen carrier. For example, a form-stable coiled collagen carrier may maintain its geometrical shape because the coating layer and/or the collagen layer has no tension acting to distort—such as uncoil—the coiled collagen carrier. A further characteristic of form-stable is that the coiled collagen carrier may be elastic deformed and revert to the shape it had before being elastic deformed by releasing the tension provided by the elastic deformation. A further characteristic of a form-stable coiled collagen carrier is that it is preferably hardened in the coiled shape.

Solid as used e.g. solid fibrinogen and solid thrombin is used in a manner being ordinary to the skilled person to mean a material in solid state. Mostly solid is preferably used to that a minor fraction of the material in question may be in a state being different from solid state (such as less than 5%, such as less than 3%, preferably less than 1%, such as less than 0.5%). Alternatively, mostly solid is preferably used to mean that the material in question may contain liquid, such as less than 5% liquid, or less than 1% liquid.

According to some preferred embodiments, the coiled collagen carrier may have a water content up to 8% and an ethanol content up to 1.6% after the coiled collagen carrier has been dried.

By the term "rolling" is meant any well known process for rolling an object i.e. by hand, mechanically or by a combination thereof.

Coiling as used e.g. in coiling said collagen carrier is preferably used to mean the process of winding the collagen carrier into an element preferably having spiral shaped cross sections. The coiled collagen carrier may have an S-shaped core.

In one embodiment according to the invention, when a collagen carrier is mechanically rolled, the process for rolling comprises the steps of gripping at least one outer edge of a collagen carrier by using at least one gripping device, such as tweezers, such as mechanical fingers, and coiling said at least one gripping device around its centre axis and thereby also coiling said collagen carrier, and releasing said mechanically rolled collagen carrier from said at least one gripping device.

The process for rolling a collagen carrier according to the invention also comprises rolling preferably a compressed collagen carrier, such as an at least partly mechanically compressed collagen carrier, such as a humidified collagen carrier, such as a humidified compressed collagen carrier. Hence, the rolling can be applied to any collagen carrier, such as a medicated sponge, which is used directly without being previously exposed to one or more physical manipulations such as e.g. humidification, compression, elevated room temperature and humidity or gamma radiation. Preferably, the rolling process can be applied to any collagen carrier which has been previously exposed to one or more of said physical manipulations. In the present context the words to roll, spool, rotate or spin are used interchangeably.

By the term "compressed collagen carrier" is preferably meant a compressed collagen carrier, which has been subjected to an evenly distributed pressure (i.e. compression) to achieve the following physical properties: a coating comprising solid fibrinogen and solid thrombin that is evenly distributed and fixed upon said collagen carrier, and having at least one of the following physical properties in the unrolled state:

I. a thickness of at the most 4 mm
II. a sterility assurance level (SAL) of $10^{-6}$.

In one embodiment of the present invention, said compressed collagen carrier has optionally been humidified either before or optionally after the compression step to at least one side of said collagen carrier. Said compressed collagen carrier has optionally been at least partly mechanically processed.

By the term "compressing" is meant the process for compressing an object such as a collagen carrier and it refers in the present context to the process when the collagen carrier when being compressed is subjected to an evenly distributed pressure. The words compression or compaction are used interchangeably. Likewise, the expressions explaining that an object can be compressed, pressed or compacted are used interchangeably herein. The collagen carrier can e.g. become compressed when it passes through a set of rollers using a certain gap size. The collagen carrier being pressed is preferably a humidified collagen carrier or a non-humidified collagen carrier. The use of a roller compactor is preferred (mechanical compression). Hence, a compression can be made by any conventional manual or mechanical way of compressing an object by subjecting it to an evenly distributed pressure i.e. preferably by passing it through a set of rollers by roller compaction, by placing the carrier between two sets of even/flat plates where the top plate is a plunger, or rolling a cylindrical object over said carrier which is placed on a flat, even bottom plate.

The expression "gap size" refers in the present context to the shortest distance measured in mm between the rollers in a roller compactor. Preferably, the compression is performed by roller compaction using a gap size between the rollers of no more than 0.30 mm, such as no more than 0.35 mm, such as no more than 0.40 mm, such as no more than 0.45 mm, such as no more than 0.50 mm, such as no more than 0.55, such as no more than 0.60 mm, such as no more than 0.65 mm, such as no more than 0.70 mm, such as preferably no more than 0.75 mm, such as no more than 0.80 mm, such as no more than 0.85 mm, such as no more than 0.90 mm, such as no more than 0.95 mm and such as no more than 1.00 mm. Using a gap size between the rollers of about 0.45-0.75 mm is preferred, such as about 0.45-0.70 mm, such as about 0.45-0.65 mm, such as about 0.45-0.60 mm, such as about 0.45-0.55 mm, such as about 0.45-0.50 mm, such as about 0.50-0.75 mm, such as about 0.55-0.75 mm, such as about 0.60-0.75 mm, such as about 0.65-0.75 mm, such as about 0.70-0.75 mm, such as about 0.50-0.70 mm, such as about 0.50-0.65 mm, such as about 0.50-0.60 mm, such as about 0.60-0.70 mm, such as about 0.60-0.65 mm. A gap size of about 0.40 mm results in a harsh/strong compression, whereas a gap size of about 0.75 mm results in a gentle compression.

Preferably, the rollers performing said roller compaction have a diameter of about 100 mm, such as about 80 mm, such as about 70 mm, such as about 38-62 mm, such as about 43-57 mm, such as preferably about 48-52 mm. Said rollers are preferably made out of an inflexible and inert material which does not transfer roller material to said compressed collagen carriers upon compaction, i.e. the surface of the rollers are important. In an embodiment, the rollers are polished.

In one embodiment, the term "rolled collagen carrier" preferably is a rolled collagen carrier characterized by the following physical properties: a coating comprising solid fibrinogen and solid thrombin that is evenly distributed and fixed upon said collagen carrier, and having at least one of the following physical properties:

I. a diameter of at the most 10 mm

II. a sterility assurance level (SAL) of $10^{-6}$.

For example, the rolled collagen carrier can have a diameter of at the most 12 mm, such as at the most 11 mm, such as at the most 10 mm, for example at the most 8 mm, such as at the most 6 mm, for example at the most 4 mm and optionally a sterility assurance level (SAL) of $10^{-6}$.

It should be noted that the rolled collagen carrier may optionally have been humidified prior to becoming rolled to at least one side of said collagen carrier (i.e. the carrier has been rolled after being humidified on at least one side), preferably to the front side comprising said coating resulting in a rolled collagen carrier having the coating externally oriented. Said rolled collagen carrier has optionally been at least partly mechanically processed, optionally also at least partly mechanically humidified.

By the term "rolled compressed collagen carrier" is meant a rolled compressed collagen carrier characterized by the following physical properties: a coating comprising solid fibrinogen and solid thrombin that is evenly distributed and fixed upon said collagen carrier, and having at least one of the following physical properties:

I. a diameter of at the most 10 mm

II. a sterility assurance level (SAL) of $10^{-6}$.

It should be noted that said rolled compressed collagen carrier may optionally have been humidified prior to becoming compressed and/or optionally at least partly mechanically rolled.

Thus, an advantage of the invention is that said rolled compressed collagen carrier is ready to use in minimally invasive surgery, such as ready to be inserted into endoscopic devices. Thus, it is preferred that the rolled compressed collagen carrier has a diameter smaller than 14 mm, such as smaller than 12 mm, smaller than 10 mm, such as smaller than 9, preferably smaller than 8, such as smaller than 7 mm By the term "mechanically rolled compressed collagen carrier" is meant a collagen carrier that has been mechanically compressed and thereafter mechanically rolled and which is characterized by the following physical properties: a coating comprising solid fibrinogen and solid thrombin that is evenly distributed and fixed upon said mechanically rolled compressed collagen carrier, and having at least one of the following physical properties:

I. a diameter of at the most 10 mm

II. a sterility assurance level (SAL) of $10^{-6}$.

Optionally, said mechanically rolled compressed collagen carrier has been mechanically humidified during processing.

By the term "humidifying or humidification" is meant the process of humidifying/moisturizing at least part of a collagen carrier with at least one liquid solvent to preferably at least one side of said carrier which has at least one side coated with a coating comprising biologically active substances. If more than one side of the carrier is coated with a coating comprising biologically active substances, then the term may comprise humidifying such as at least two sides, such as at least three sides, such as at least four sides, such as at least five sides, such as all sides of said collagen carrier. The humidified side is preferably the side comprising a coating, but it may also be a side that does not comprise a coating.

Humidifying as used in e.g. humidifying at least a part of said collagen carrier is preferably also used to mean the step of applying a liquid substance to a collagen carrier.

A device for applying moisture is used to characterise a device that humidifies at least a part of a collagen carrier. It is noted that moisture is used in a broad context and is not limited to water vapour or water in general. In particular, the solvent applied is preferably a solvent not being water or contains less than 2.4% w/w, such as less than 1% w/w, such as less than 0.5 w/w % of water, as disclosed below with respect to preferred solvents.

Thus, the term "humidified collagen carrier" is meant to mean a collagen carrier that has been exposed to at least one liquid solvent to preferably at least one side of said carrier, such as at least two sides, such as at least three sides, such as at least four sides, such as at least five sides, such as all sides, to achieve a humidified collagen carrier.

In one embodiment of the present invention the collagen carrier is preferably humidified on at least one side of said carrier (i.e. the front) which has at least one side coated with a coating comprising biologically active substances before being compressed and/or before being rolled. The words humidified and moisturized are used interchangeably. In another embodiment it is preferred to humidify both the front and back of a collagen carrier of the present invention, wherein the front comprises said coating. Said humidified collagen carrier has optionally been at least partly mechanically processed.

In an embodiment of the present invention said humidified collagen carrier has a coating comprising solid fibrinogen and solid thrombin that is evenly distributed and fixed upon said collagen carrier, and having at least one of the following physical properties:

I. a diameter of at the most 10 mm

II. a sterility assurance level (SAL) of $10^{-6}$.

By the term "solvent" is meant any suitable solvent such as physiological saline, purified water, aqueous vapour or any suitable organic solvent such as ethanol, dehydrated ethanol with a maximum content of 0.1% water, isopropanol or methanol. An alcohol is selected from the group consisting of ethanol, dehydrated ethanol with a maximum content of 0.1% water, 1-propanol, 2-propanol, 2-methyl-2-propanol, ethylene glycol, 1-butanol, 2-butanol or any combination thereof. In an embodiment a solvent is selected from ethanol, dehydrated ethanol with a maximum content of 0.1% water, isopropanol, 1-propanol, 2-methyl-2-propanol, water or any combination thereof. In a further embodiment, a solvent is selected from ethanol, dehydrated ethanol with a maximum content of 0.1% water, isopropanol, water or combinations thereof. In a embodiment the ethanol is dehydrated ethanol with a maximum content of 0.1% water. In one embodiment of the applied solvent, the amount of applied solvent is about 0.8-10.75 mg/cm$^2$ collagen carrier, such as about 1.2-10.75 mg/cm$^2$ collagen carrier, such as about 0.8-10.4 mg/cm$^2$ collagen carrier, such as about 0.8-6.1 mg/cm$^2$ collagen carrier, such as about 1.2-4.7 mg/cm$^2$ collagen carrier, such as about 2.85-4.24 mg/cm$^2$. An alcohol—preferably ethanol—is a preferred solvent. In an embodiment, the solvent essentially consist of a mixture of ethanol or dehydrated ethanol with a maximum content of 0.1% water and water or isopropanol and water, wherein the amount of water is up to 20%, such as up to 18%, such as up to 16%, such as up to 14%, such as up to 12%, such as up to 10%, such as up to 8%, such as up to 6%, such as up to 5%, such as up to 4%, such as up to 3%, such as 2.4%, such as up to 2%, such as up to 1.5%, such as up to 1%, such as up to 0.5%. The solvent may also contain fibrinogen and/or thrombin and/or albumin and/or some salt. In a further embodiment, ethanol or dehydrated ethanol with a maximum content of 0.1% water is the preferred solvent and is used in an amount of about 9 mg ethanol/cm$^2$ collagen carrier, such as about 8 mg ethanol/cm$^2$ collagen carrier, such as about 7 mg ethanol/cm$^2$ collagen carrier, such as about 6 mg ethanol/cm$^2$ collagen carrier, such as about 5 mg ethanol/cm$^2$ collagen carrier, such as about 4 mg ethanol/cm$^2$ collagen carrier, such as about 3 mg ethanol/cm$^2$ collagen carrier, such as about 2 mg ethanol/cm$^2$ collagen carrier, such as about 1.2 mg ethanol/cm$^2$ collagen carrier, such as about 1 mg ethanol/cm$^2$ collagen carrier, such as about 0.5 mg ethanol/cm$^2$ collagen carrier.

Without being bound by theory, it is speculated that using more than about 10.75 mg ethanol or dehydrated ethanol with a maximum content of 0.1% water/cm$^2$ collagen carrier, such as about 10.4, mg ethanol/cm$^2$ collagen carrier could make said collagen carriers become sticky when being compressed. Hence, using an ethanol level of no more than 10.75 mg ethanol/cm$^2$ collagen fleece is preferred.

By the term "relative humidity (RH)" is meant the amount of water vapor in a mixture of air and water vapor.

In an embodiment, the process according to the present invention is performed at 10-75% RH, such as 30-50% RH, such as 30-60%, such as 30-64% RH, such as 30-65% RH, such as 30-70% RH, such as 40-60% RH, such as 40-64% RH, such as 40-70% RH and optionally at a temperature of 5-30° C., such as 18-22° C., such as 18-25° C. In a preferred embodiment, RH is 30-50% and the temperature is 18-22° C. which is the preferred relative humidity range and temperature range of the room (e.g. manufacturing facility) where the rolled and/or compressed collagen carriers are processed. See further below when the term "drying" is defined. In another embodiment the relative humidity range and temperature of the room (e.g. manufacturing facility) where the rolled and/or compressed collagen carriers are processed is about 25° C. and 64-70% RH.

By the term "density" or the mass density of a material is meant the material's mass per unit volume. The symbol most often used for density is p but in the present context, density is defined as weight per unit volume mg/cm$^3$, which is also called specific weight. The method and the equipment used for determining the density are disclosed in further detail in the example section below. The density of a collagen carrier according to the present invention is the density of the collagen carrier excluding the coating layer. In an embodiment of the present invention, the density of the collagen carrier before humidification and/or rolling and/or compression, such as for the collagen carrier provided in step (a) of the present invention, is in the range of 1-10 mg/cm$^3$, such as in the range of 1-9 mg/cm$^3$, such as in the range of 1-8 mg/cm$^3$, such as in the range of 1-7 mg/cm$^3$, such as in the range of 1-6 mg/cm$^3$, such as in the range of 1-5 mg/cm$^3$, such as in the range of 1-4 mg/cm$^3$, such as in the range of 1-3 mg/cm$^3$, such as in the range of 1-2 mg/cm$^3$, such as in the range of 2-9 mg/cm$^3$, such as in the range of 2-8 mg/cm$^3$, such as in the range of 2-7 mg/cm$^3$, such as in the range of 2-6 mg/cm$^3$, such as in the range of 2-5 mg/cm$^3$, such as in the range of 2-4 mg/cm$^3$, such as in the range of 3-9 mg/cm$^3$, such as in the range of 3-8 mg/cm$^3$, such as in the range of 3-7 mg/cm$^3$, such as in the range of 3-6 mg/cm$^3$, such as in the range of 3-5 mg/cm$^3$, preferably such as in the range of 3.0-4.5 mg/cm$^3$, such as in the range of 3.0-4.4 mg/cm$^3$, such as in the range of 3.0-4.3 mg/cm$^3$, such as in the range of 3.0-4.2 mg/cm$^3$, such as in the range of 3.0-4.1 mg/cm$^3$, such as in the range of 3.0-4.0 mg/cm$^3$, such as in the range of 3.0-3.9 mg/cm$^3$, such as in the range of 3.0-3.8 mg/cm$^3$, such as in the range of 3.0-3.7 mg/cm$^3$, such as in the range of 3.0-3.6 mg/cm$^3$, such as in the range of 3.0-3.5 mg/cm$^3$, such as in the range of 3.0-3.4 mg/cm$^3$, such as in the range of 3.0-3.3 mg/cm$^3$, such as in the range of 3.0-3.2 mg/cm$^3$, such as in the range of 3.0-3.1 mg/cm$^3$, such as in the range of 3.1-4.5 mg/cm$^3$, such as in the range of 3.2-4.5 mg/cm$^3$, such as in the range of 3.3-4.5 mg/cm$^3$, such as in the range of 3.4-4.5 mg/cm$^3$, such as in the range of 3.5-4.5 mg/cm$^3$, such as in the range of 3.6-4.5 mg/cm$^3$, such as in the range of 3.7-4.5 mg/cm$^3$, such as in the range of 3.8-4.5 mg/cm$^3$, such as in the range of 3.9-4.5 mg/cm$^3$, such as in the range of 4.0-4.5 mg/cm$^3$, such as in the range of 4.1-4.5 mg/cm$^3$, such as in the range of 4.2-4.5 mg/cm$^3$, such as in the range of 4.3-4.5 mg/cm$^3$, such as in the range of 4.4-4.5 mg/cm$^3$.

The density of a humidified and/or compressed and/or rolled collagen carrier of the present invention is preferably in the range of 1-15 mg/cm$^3$, such as in the range of 2-15 mg/cm$^3$, such as in the range of 3-15 mg/cm$^3$, such as in the range of 4-15 mg/cm$^3$, such as in the range of 5-15 mg/cm$^3$, such as in the range of 6-15 mg/cm$^3$, such as in the range of 7-15 mg/cm$^3$, such as in the range of 8-15 mg/cm$^3$, such as in the range of 9-15 mg/cm$^3$, such as in the range of 10-15 mg/cm$^3$, such as in the range of 11-15 mg/cm$^3$, such as in the range of 12-15 mg/cm$^3$, such as in the range of 13-15 mg/cm$^3$, such as in the range of 14-15 mg/cm$^3$, such as in the range of 3-14 mg/cm$^3$, such as in the range of 3-12 mg/cm$^3$, such as in the range of 3-10 mg/cm$^3$, such as in the range of 3-9 mg/cm$^3$, such as in the range of 3-8 mg/cm$^3$, such as in the range of 3-7 mg/cm$^3$, such as in the range of 3-6 mg/cm$^3$, such as in the range of 3-5 mg/cm$^3$, such as in the range of 3.0-4.5 mg/cm$^3$, such as in the range of 3.0-4.4 mg/cm$^3$, such as in the range of 3.0-4.3 mg/cm$^3$, such as in the range of 3.0-4.2 mg/cm$^3$, such as in the range of 3.0-4.1 mg/cm$^3$, such as in the range of 3.0-4.0 mg/cm$^3$, such as in the range of 3.0-3.9 mg/cm$^3$, such as in the range of 3.0-3.8 mg/cm$^3$, such as in the range of 3.0-3.7 mg/cm$^3$, such as in the range of 3.0-3.6 mg/cm$^3$, such as in the range of 3.0-3.5 mg/cm$^3$, such as in the range of 3.0-3.4 mg/cm$^3$, such as in the range of 3.0-3.3 mg/cm$^3$, such as in the range of 3.0-3.2 mg/cm$^3$, such as in the range of 3.0-3.1 mg/cm$^3$, such as in the range of 3.1-4.5 mg/cm$^3$, such as in the range of 3.2-4.5 mg/cm$^3$, such as in the range of 3.3-4.5 mg/cm$^3$, such as in the range of 3.4-4.5 mg/cm$^3$, such as in the range of 3.5-4.5 mg/cm$^3$, such as in the range of 3.6-4.5 mg/cm$^3$, such as in the range of 3.7-4.5 mg/cm$^3$, such as in the range of 3.8-4.5 mg/cm$^3$, such as in the range of 3.9-4.5 mg/cm$^3$, such as in the range of 4.0-4.5 mg/cm$^3$, such as in the range of 4.1-4.5 mg/cm$^3$, such as in the range of 4.2-4.5 mg/cm³, such as in the range of 4.3-4.5 mg/cm³, such as in the range of 4.4-4.5 mg/cm³.

The density of a humidified and/or compressed and rolled collagen carrier of the present invention is measured upon unrolling said rolled collagen carrier of the present invention. Please note that the density of a collagen carrier of the present invention is the density of the collagen carrier excluding the coating layer.

It is presently preferred to determine the density by weighing a collagen carrier of known volume, such as a rolled and/or compressed collagen carrier of a certain size (see the examples section), such as a large size collagen carrier (also called a strip or a fleece). The density is calculated by dividing the mass of the collagen carrier by the volume of the collagen carrier. The method and the equipment used for determining the density are disclosed in further detail in the example section below.

By the term "coating" is preferably meant a coating either comprising or essentially consisting of the biologically active substances fibrinogen and thrombin that are evenly distributed and fixed upon at least one side of a collagen carrier of the present invention, such as a rolled and/or compressed collagen carrier, such as an unrolled rolled and/or compressed collagen carrier. The coating may also include e.g. riboflavin (yellow color as marker of coated area). In one embodiment of the present invention, the active substances are preferably solid human fibrinogen, solid human thrombin and optionally solid riboflavin. Thus in one embodiment of the invention, the coating essentially consists of solid human fibrinogen, solid human thrombin and solid riboflavin. The coating is present on at least one side of the collagen carrier, such as a rolled and/or compressed collagen carrier, such as an unrolled rolled and/or compressed collagen carrier. Hence, in one embodiment the collagen carrier, such as a rolled and/or compressed collagen carrier, such as an unrolled rolled and/or compressed collagen carrier comprises one or more active sides wherein fibrinogen is present in an amount of 1.3-10 mg/cm², such as 2-10 mg/cm², such as 4.3-6.7 mg/cm², preferably about 3.6-7.4 mg/cm², such as about 5.5 mg/cm², and thrombin is present in an amount of 0.9-20 IU/cm², such as 0.9-15 IU/cm², such as 0.9-10 IU/cm², such as 1.0-5.5 IU/cm², preferably such as about 1.3-2.7 IU/cm², such as about 2.0 IU/cm². Said coating is preferably applied to at least one side of said collagen carrier, such as a rolled and/or compressed collagen carrier, such as an unrolled rolled and/or compressed collagen carrier.

When the collagen carrier, such as a rolled and/or compressed collagen carrier, such as an unrolled rolled and/or compressed collagen carrier, has a coating on one side of said carrier and when it is rolled the side coated with the biologically active substances can be externally oriented on said rolled collagen carrier, or the side coated with the biologically active substances can be internally oriented on the rolled collagen carrier. Presently, the first alternative is preferred for a rolled compressed collagen carrier of the present invention, i.e. external orientation of said coating.

By the term "diameter" of e.g. the rolled collagen carrier is meant the diameter of the cross section of any type of collagen carrier that has been rolled or coiled according to the present invention. Thus, the diameter of the resulting rolled collagen carrier as measured on the cross section (e.g. the shortest side) is about 5-12 mm, such as about 6-11, such as about 7-10 mm, such as about 8-9 mm, such as at the most 11 mm, preferably such as at the most 10 mm, preferably such as at the most 9 mm, such as at the most 8 mm, such as at the most 7 mm, such as at the most 6 mm, such as at the most 5 mm, such as at the most 4.5 mm, such as at the most 4 mm, such as at the most 3.5 mm, such as at the most 3 mm, such as at the most 2.5 mm, such as at the most 2.0 mm, such as at the most 1.5 mm, such as at the most 1.0 mm. The preferred diameter is less than 10 mm for midi sized fleeces, i.e. midi sized fleeces have the dimensions 46-49 mm*46-50 mm*4-7 mm.

By the term "thickness" is meant the shortest measurable distance across any collagen carrier of the invention that is unrolled or nonrolled, which means that the thickness depends on whether the collagen carrier has been previously rolled or not and/or whether it has been previously compressed, humidified or not. When the term thickness is used to describe any type of unrolled or nonrolled collagen carrier according to the present invention the thickness is meant to mean the thickness which is about 1-10 mm, such as about 2-8, such as about 4-6, such as at the most 10 mm, such as at the most 9 mm, such as at the most 8 mm, such as at the most 7 mm, such as at the most 6 mm, such as at the most 5 mm, such as at the most 4 mm, such as at the most 3 mm, such as at the most 2 mm, such as at the most 1 mm. In an embodiment the preferred thickness of a collagen carrier is 4-7 mm. In another embodiment, the preferred thickness of an unrolled collagen carrier is at the most 4 mm.

By the term "sterility assurance level (SAL)" is meant a term used in microbiology to describe the probability of a single unit being non-sterile after it has been subjected to a sterilization process. For example, medical device manufacturers design their sterilization processes for an extremely low SAL leading to a $10^{-6}$ microbial survivor probability, i.e. assurance of less than or equal to 1 chance in 1 million that viable microorganisms are present in the sterilized device, as defined in USP 34 <1211> (United States Pharmacopeia version 32, chapter 1211. SAL is also used to describe the killing efficacy of a sterilization process, where a very effective sterilization process has a very low SAL.

Sterilisation can occur before and/or after any packaging steps.

Gamma radiation can be used as a sterilization method to kill living organisms in a process called irradiation. Applications of irradiation include sterilizing medical equipment as an alternative to autoclaves or chemical means. In one embodiment of the present invention, a collagen carrier, such as a rolled and/or compressed collagen carrier, is subjected to gamma radiation. The gamma radiation may reduce the adhesion of the collagen carrier, such as no more than 0.5%, such as no more than 1%, such as no more than 2%, such as no more than 3%, such as no more than 4%, such as no more than 5%, such as no more than 6%, such as no more than 7%, such as no more than 8%, such as no more than 9%, such as preferably no more than 10%, such as no more than 11%, such as no more than 12%, such as no more than 13%, such as no more than 14%, such as no more than 15%, such as no more than 16%, such as no more than 17%, such as no more than 18%, such as no more than 19%, such as no more than 20%, such as no more than 25%. This was evaluated in vitro by visual inspection of adherence of a rolled collagen carrier according to the invention on liver tissue. Fibrinogen is preferably present in an amount of 2-10 mg/cm² and thrombin is preferably present in an amount of 1.0-5.5 IU/cm² after the irradiation process and it is preferred that the levels may exceed their respective levels such as no more than 0.5%, such as no more than 1%, such as no more than 2%, such as no more than 3%, such as no more than 4%, such as no more than 5%, such as no more than 6%, such as no more than 7%, such as no more than 8%, such as no more than 9%, such as preferably no more than 10%, such as no more than 11%, such as no more than 12%, such as no more than 13%, such as no more than 14%, such as no more than 15%, such as no more than 16%, such as no more than 17%, such as no more than 18%, such as no more than 19%, such as no more than 20%, such as no more than 25%. It is noted that "exceeding their respective levels" means that the values may either increase or decrease.

It is preferred that the rolled and/or compressed collagen carrier can be stored for an acceptable duration of time whilst maintaining their biological and physiochemical properties, i.e. preferably, storage neither affects the physical and chemical properties of said rolled and/or compressed collagen carrier nor the in vitro adherence (to liver tissue) of the rolled and/or compressed collagen carriers. An acceptable shelf-life is preferably up to 60 months, such as up to 54 months, such as up to 48 months, such as up to 42 months, such as up to 36 months, such as up to 30 months, such as up to 24 months, such as up to 18 months, such as up to 12 months, such as up to 6 months, such as up to 5 months, such as up to 4 months, such as up to 3 months, such as up to 2 months, such as up to 1 month. Hence, it is preferred that rolled and/or compressed collagen carriers of the present invention are stable.

By the word "stable" is meant that said rolled and/or compressed collagen carriers are physiochemical and biologically stable meaning that they retain the same properties as they had when they were prepared. Hence, said rolled and/or compressed collagen carriers retain their stability under transport, warehousing (storage), logistics, sales, and up to and including the end use of said rolled and/or compressed collagen carriers i.e. the collagen carriers maintain regulations and all end-use requirements.

By the term "drying" is meant any well known method of drying an object such as by passive evaporation, desiccation, blowing air with a humidity lower than the object that needs drying over said object, applying heat etc. In one embodiment drying is performed in a drying tunnel i.e. tunnel comprises a conveyor belt transporting the trays that contains the rolled collagen carriers through the tunnel with an airflow securing the drying. In one embodiment the passage through the tunnel, i.e. the length of the drying takes around 30 min. In another embodiment the drying tunnel dries off the solvent such as dries off ethanol, e.g. dries off isopropanol, e.g. dries off isopropanol and ethanol. Water is dried off using a desiccant, such as e.g. silica gel. The drying off of water may take up to about 48 hours, such as up to about 36 hours, such as up to about 24 hrs, such as up to about 18 hours, such as up to about 12 hours, such as up to about 6 hours, such as up to about 2 hours. The drying off of water preferably takes up to about 24 hours.

Silica gel is preferably used to mean a granular, vitreous, porous form of silicon dioxide made synthetically from sodium silicate. Silica gel is a commonly used desiccant as beads packed in a permeable bag.

Endoscopic instrument: by "endoscopic instrument" is meant herein any endoscopic instrument known to one skilled in the art, for example endoscopic grab tongs, endoscopic pincet, endoscopic dissector, endoscopic forceps, Johansons clamp or other endoscopic clamp, endoscopic scissors, an endoscopic grasper, two or more graspers, laparoscopic swabs (preferably fastened to long pins or fixed to graspers), or another suitable endoscopic instrument.

In one embodiment of the present invention, the drying of an optionally humidified rolled and/or compressed collagen carrier according to the invention neither affects the physical and chemical properties of said collagen carrier nor the in vitro adherence (to liver tissue) of said collagen carrier. In one embodiment of the present invention, an optionally humidified rolled and/or compressed collagen carrier is dried by passive evaporation of a solvent, preferably ethanol, by controlling the room temperature and room humidity to within the ranges of which is 3-35° C., 5-80% RH, such as 13-35° C., 36-65% RH, such as 23-35° C., 36-65% RH, such as 33-35° C., 36-65% RH, such as 3-25° C., 36-65% RH, such as 3-15° C., 36-65% RH, such as 3-5° C., 36-65% RH, preferably 18-22° C., 40-60% RH, such as 18-22° C., 36-65% RH, such as at 20-25° C., 40-60% RH, such as at 22-25° C., 40-60% RH, such as at 24-25° C., 40-60% RH, such as at 18-23° C., 40-60% RH, such as at 18-21° C., 40-60% RH, such as at 18-19° C., 40-60% RH, such as at 18-25° C., 35-60% RH, such as at 18-25° C., 30-60% RH, such as at 18-25° C., 40-65% RH, such as at 18-25° C., 40-70% RH, such as at 18-25° C., 40-75% RH, such as at 18-25° C., 40-80% RH, such as at 18-25° C., 45-80% RH, such as at 18-25° C., 50-80% RH, such as at 18-25° C., 55-80% RH, such as at 18-25° C., 60-80% RH, such as at 18-25° C., 65-80% RH, such as at 18-25° C., 70-80% RH, such as at 18-25° C., 75-80% RH. Said optionally humidified rolled and/or compressed collagen carrier is preferably dried 30 minutes by blowing air with a humidity lower than said collagen carrier (such as a rolled and/or compressed collagen carrier that needs drying) over said collagen carrier followed by passive evaporation of the solvent by placing said collagen carrier in a desiccator.

After the coiled collagen carriers has been dried in e.g. the drying tunnel for preferably about 30 minutes, the coiled collagen carriers may be further dried e.g. by arranging the coiled collagen carriers in a sealed box together with a desiccant. The coiled collagen carriers are preferably present in the sealed box for up to 72 hours.

A drying time of up to 72 hours, such as up to 48 hours, preferably up to 24 hours is preferred, such as up to 20 hours, such as up to 15 hours, such as up to 10 hours, such as up to 5 hours, such as up to 1 hour, such as up to 50 minutes, such as up to 40 minutes, preferably such as up to 30 minutes, such as up to 20 minutes, such as up to 10 minutes, such as up to 5 minutes, such as up to 1 minute, such as up to 50 seconds, such as up to 40 seconds, such as up to 30 seconds, such as up to 20 seconds, such as up to 10 seconds, such as up to 5 seconds.

A residual amount of the applied at least one liquid solvent to the collagen carrier, such as a rolled and/or compressed collagen carrier is acceptable such as no more than 0.1% w/w, or such as no more than 0.2% w/w, or such as no more than 0.5% w/w, or such as no more than 0.8% w/w or such as no more than 1.0% w/w, or such as no more than 1.2% w/w, or such as no more than 1.4% w/w, or preferably such as no more than 1.6% w/w, or such as no more than 1.8% w/w, or such as no more than 2.0% w/w, or such as no more than 2.5% w/w, or such as no more than 3.0% w/w, or such as no more than 3.5% w/w, or such as no more than 4.0% w/w, or such as no more than 5.0% w/w, or such as no more than 8.0% w/w, or such as no more than 10.0% w/w, or such as no more than 12.5% w/w, or such as no more than 15.0% w/w, or such as no more than 17.5% w/w, or such as no more than 20.0% w/w, or such as no more than 22.5% w/w, or such as no more than 25.0% w/w, or such as no more than 27.5% w/w, or such as no more than 30.0% w/w, or such as no more than 32.5% w/w, or such as no more than 35.0% w/w. When the applied liquid solvent is ethanol, no more than 1.6% w/w residual ethanol is preferred and/or when the applied liquid solvent is water no more than 8.0% w/w residual water is preferred, preferably such as no more than 5.0% w/w. A residual amount of the applied at least one liquid solvent, such as at least two liquid solvents, such as at least three liquid solvents to the collagen carrier, such as a rolled and/or compressed collagen carrier is acceptable.

It may happen that one or more solvents or moisture from the room (aqueous vapour) is absorbed passively by a collagen carrier, such as a rolled and/or compressed collagen carrier during processing. In one embodiments, if such passive absorption of moisture, such as water, has taken place a residual amount of said moisture is acceptable such as no more than 0.1% w/w, such as no more than 0.2% w/w, such as no more than 0.5% w/w, such as no more than 0.8% w/w such as no more than 1.0% w/w, such as no more than 1.2% w/w, such as no more than 1.4% w/w, such as no more than 1.6% w/w, such as no more than 1.8% w/w, such as no more than 2.0% w/w, such as no more than 2.5% w/w, such as no more than 3.0% w/w, such as no more than 3.5% w/w, such as no more than 4.0% w/w, preferably such as no more than 5.0% w/w, such as no more than 8.0% w/w, such as no more than 10.0% w/w, such as no more than 12.5% w/w, such as no more than 15.0% w/w, such as no more than 17.5% w/w, such as no more than 20.0% w/w, such as no more than 22.5% w/w, such as no more than 25.0% w/w, such as no more than 27.5% w/w, such as no more than 30.0% w/w, such as no more than 32.5% w/w, such as no more than 35.0% w/w. When the passively absorbed solvent is water no more than 8.0% w/w residual water is preferred, preferably such as no more than 5.0% w/w. Residual solvent is measured by conventional methods known to the person skilled in the art, such as by using gas chromatography (GC). GC is a common type of chromatography used in analytical chemistry for separating and analyzing compounds that can be vaporized without decomposition. In the present invention, GC is used to determine one or more solvents or moisture from the room (aqueous vapour) in the collagen carrier.

By the term "sterilizing" is meant any well-known method of sterilizing an object such as in the present invention a collagen carrier, such as a rolled and/or compressed collagen carrier. Any such appropriate sterilization method should result in the required probability of a single unit being non-sterile after it has been subjected to the sterilization process. Hence, preferably not more than one collagen carrier, such as a rolled and/or compressed collagen carrier in a million should be nonsterile after the sterilization process. An example of a sterilization process is gamma radiation. Sterilization can also be achieved by applying the proper combinations of heat, chemicals, irradiation, and high pressure, but these are less preferred methods. In a preferred embodiment the sterilization is performed using gamma irradiation.

By the term "packing" is meant any well-known method of packaging an object such as in the present invention a collagen carrier, such as a rolled and/or compressed collagen carrier. Packaging and packing are words that are used interchangeably within this context. Packaging is meant to mean a coordinated system of preparing goods for transport, warehousing, logistics, sales, and end use. Packaging can for example contain, protect, preserve, transport, inform, and sell an object, preferably such an object as the collagen carrier, such as a rolled and/or compressed collagen carrier of the present invention. A suitable container is used for packing the collagen carrier, such as a rolled and/or compressed collagen carrier of the present invention.

By the term "suitable container" is meant in one embodiment any container that is suitable for transport, warehousing (storage), logistics, sales, and for the end use of a collagen carrier, such as a rolled and/or compressed collagen carrier of the present invention. Hence, said suitable container encloses and/or protects said collagen carrier. Thus preferably said collagen carrier, such as a rolled and/or compressed collagen carrier retains its properties substantially as they were at the time of packaging. An example of a suitable container is a tray made of PET (polyethylene terephthalate) or polystyrene shaped to fit the rolled collagen carrier of the present invention. A suitable container according to the present invention is further sealed with a lid, such as e.g. a Tyvec lid. In an embodiment of the invention, the closed tray with a lid is further placed inside a double aluminium foil, preferably with a desiccant. In an even further embodiment of the invention, the double aluminium foil is marked to indicate that the content has been sterilized (see further below). Other suitable containers are well known in the art.

In an embodiment package testing is conducted and documented to ensure that packages meet regulations and all end-use requirements. Manufacturing processes are controlled and validated to ensure consistent performance.

Preferably, a suitable container of the present invention is sterilized in the package. Medical device packaging is highly regulated and the sterility must be maintained throughout distribution to allow immediate use by physicians. A series of special packaging tests is well known in the art and used to measure the ability of the package to maintain sterility. Relevant standards include: ASTM D1585—Guide for Integrity Testing of Porous Medical Packages, ASTM F2097—Standard Guide for Design and Evaluation of Primary Flexible Packaging for Medical Products, EN 868 Packaging materials and systems for medical devices which are to be sterilized. General requirements and test methods, ISO 11607 Packaging for terminally sterilized medical devices, and others.

In an embodiment the container is a foil packaging material, such as a single or double aluminium foil or a plastic packaging material, such as a polystyrene or PET (polyethylene terephthalate) or a combination of a foil and plastic packaging material, such as a single or double aluminium foil and as a polystyrene or PET (polyethylene terephthalate).

By the term "weight-weight percentage" or "% w/w" is meant grams substance per grams of another substance in percent (per 100 gram). Thus, if e.g. residual water is present in an amount of 2% w/w in a collagen carrier, it is meant to mean 2 grams of water is present with 98 grams of collagen carrier. The total weight will be 100 grams of the collagen carrier including the residual water but the volume of the 100 grams of residual may be different from 100 ml.

Note that by the "weight" of the collagen carriers is meant the weight of the collagen carrier excluding the weight of the coating layer.

It should be noted that embodiments and features described in the context of one of the aspects of the present invention also apply to the other aspects of the invention i.e. all aspects relating to a rolled compressed collagen carrier also apply to a compressed collagen carrier or a rolled collagen carrier or an unrolled rolled compressed collagen carrier or a coiled collagen carrier (as the terms "coiled" and "rolled" are used interchangeably herein), and similarly for the process aspects.

An aspect of the present invention relates to a process for coiling a collagen carrier, the collagen carrier comprising (i)

a collagen layer and (ii) a coating layer comprising fibrinogen and thrombin, said process comprising the sequential steps of:
  humidifying at least part of said collagen carrier,
  coiling said collagen carrier by gripping the collagen carrier between a pair of elongated members, and rotating the pair of elongated members about an axis being parallel to a longitudinal extension of the elongate members in order to coil the collagen carrier on the members, while the collagen carrier is supported by a support device,
  drying the coiled collagen carrier,
thereby providing a form-stable coiled collagen carrier.

Another aspect of the present invention relates to a process for coiling a collagen carrier, the collagen carrier comprising (i) a collagen layer and (ii) a coating layer preferably comprising fibrinogen and thrombin, said process comprising the sequential steps of:
  humidifying at least part of said collagen carrier,
  coiling said collagen carrier
  drying the coiled collagen carrier,
thereby providing a form-stable coiled collagen carrier.

Any type of fibrinogen and/or thrombin can be used in the coating layer, preferably the fibrinogen and/or thrombin used in the coating layer is mostly solid and/or solid. It is preferred that the fibrinogen and/or thrombin are dry. Preferably, said sequential steps are consecutive steps. In an embodiment of the present invention, the process consists of the above-mentioned process steps. In another embodiment, the process comprises or consists of the above-mentioned process steps and a further packing step wherein the coiled product is sealed in a container, and sterilized. In an embodiment of the present invention, the coiling is performed by gripping the collagen carrier using at least one gripping device. In an embodiment of the present invention, the coiling is performed by gripping the collagen carrier using at least one pair of tweezers or pincers.

The drying of the coiled collagen carrier can be done using any suitable drying process, such as e.g. by blowing air with a humidity lower than the coiled collagen carrier and optionally applying heat to the air. Preferably, said drying is at least 5 minutes long, such as between 5 minutes and 1 hour, such as between 20 minutes and 40 minutes long, such as between 25 and 35 minutes long. A ventilation tunnel can for example be used for the drying step.

Any surface of the collagen carrier can be humidified. Preferably, at least the coating layer of said collagen carrier is humidified. In one embodiment of the present invention only the coating layer is humidified, in another embodiment of the invention both the top and bottom sides of the collagen carrier are humidified. In another embodiment of the present invention, the surface humidified is the collagen layer.

Preferably, the collagen carrier is humidified by a solvent. Any suitable solvent can be used, such as an organic solvent or water. In an embodiment of the present invention, the solvent comprises or consists of ethanol, such as dehydrated ethanol with a maximum content of 0.1% water. In another embodiment, the solvent comprises or consists of ethanol, such as dehydrated ethanol with a maximum content of 0.1% water, and water. The solvent can also comprise or consist of isopropanol. The solvent can alternatively be a mixture of at least 70% ethanol such as dehydrated ethanol with a maximum content of 0.1% water and another solvent (such as water), such as at least 80% ethanol, such as at least 90% ethanol, such as at least 95% ethanol. The solvent can in another embodiment be a mixture of at least 80% isopropanol and another solvent (such as water), such as at least 90% or 95% isopropanol. The solvent can also comprise fibrinogen and/or thrombin and/or other factors. In a preferred embodiment the ethanol may be dehydrated ethanol with a maximum content of 0.1% water.

In an embodiment of the present invention, the rolling/coiling up step is performed after the coating layer has been softened.

Preferably, the coating layer of the collagen carrier is humidified using a solvent. In an embodiment of the present invention, the collagen carrier is humidified on the coating layer by a solvent in an amount between 0.1 and 25 cm$^2$ surface of the coating layer, such as e.g. 1.2-10.75 mg/cm$^2$ surface of the coating layer. For rolled versions of the standard TachoSil® sizes available on the market (such as e.g. midi sized fleeces), the following solvent amounts are preferred on the coating layer: 30-160 mg solvent (such as ethanol) per collagen carrier, such as 30-100 mg solvent (such as ethanol) per collagen carrier, such as preferably 90-100 mg solvent (such as ethanol) per collagen carrier, such as for a collagen carrier with a 25 cm$^2$ coating surface such as for the small or midi sized Tachosil® collagen carrier. In an embodiment of the present invention, the solvent comprises or consists of ethanol or dehydrated ethanol with a maximum content of 0.1% water.

In an embodiment of the process for coiling a collagen carrier, the process further comprises the step of compressing the collagen carrier to reduce the thickness of the collagen carrier. For example, the collagen carrier can be compressed with a compression ratio between 2 and 18, such as e.g. 4-14, such as preferably between 6-12. The compression step can in one embodiment be performed by passing the humidified collagen carrier through a set of rollers having a gap size being smaller than the thickness of the collagen carrier before passing through the set of rollers. An example gap size is between 0.2 mm and 2 mm, such as e.g. 0.4-1.6 mm, such as between 0.5-1.0 mm, or no more than 0.75 mm, such as e.g. 0.5-0.75. One preferred gap size is 0.6 mm. The compression is preferably performed prior to the coiling of the collagen carrier.

The compression device may preferably include a certain flexibility allowing the compression ratio to be influenced by the collagen carrier and rendering the compression device more suited for handling collagen carriers of different densities. In embodiments where the compression device comprises a set of rollers, this is implemented by allowing the rollers to move apart each other so that the gap size increases. The movement of the rollers to increase the gap size is caused by the collagen carrier pressing on the surface of the rollers during it passage through the gap. Mechanically this may preferably be implemented by allowing some flexibility in the means used for mounting the rollers or by mounting one or both rollers in a manner allowing displacement of the rollers in a direction being perpendicular to the axis of rotation and biasing the rollers towards each other by springs.

During the drying step of the coiling process, the coiled collagen carrier can be supported by a support device, e.g. by contacting the support device. For example, at least an edge of the coiled collagen carrier is fixed by the support device relatively to the coiled collagen carrier during drying, i.e. the edge of the coiled collagen carrier is pushed against the support device. The support device can be any suitable shape, such as e.g. a "U" shape, a rounded shape, a tubular shape or any other shape capable of supporting and maintaining the coiled shape of the collagen carrier while it is drying, prior to the product becoming form-stable in the dry state. In one preferred embodiment, the support device is a cavity shaped as a segment of a cylinder having at least one open end, and wherein the curved part of the cylinder segment extends at least 180° (see e.g. FIG. 1). In one embodiment of the present invention, the edge of the coiled collagen carrier is arranged inside the segment of the cylinder and the edge abuts the inner surface of the cylinder.

Preferably, the process of the present invention further comprises the step of extracting the elongated members from the coiled collagen carrier. For example, the extraction of the elongated members is performed before drying of the coiled collagen carrier. The elongated members can be a pair of tweezers, so for example the extraction of the at least one pair of tweezers can be performed before drying of the coiled collagen carrier. Preferably the elongated members form a gripping device.

In an embodiment of the present invention, the process further comprises the step of arranging the form-stable coiled collagen carrier in a container and subsequently sealing the container. For example, the coiled carrier can be arranged in an inner container and the inner container can be arranged in an outer container, further optionally comprising the step of arranging a desiccator inside the outer container prior to sealing of the container.

The process of the present invention preferably comprises the step of sterilizing the coiled collagen carrier. This can for example be done using gamma radiation. One embodiment of the present invention comprises the step of sterilizing the coiled collagen carrier to a sterility assurance level (SAL) of $10^{-6}$ using gamma radiation.

The process of the present invention can comprise a step wherein a label with information relating to the product of the present invention, such as e.g. relating to the sterilization level, is placed on the outside of the outer container.

In one embodiment of the present invention, the process for coiling a collagen carrier has the feature that the atmosphere surrounding the collagen carrier and humidification device while being humidified, compressed and coiled, is maintained at a set temperature and/or humidity. The temperature and/or humidity can for example be in the range of 10-40° C. and 10-70% RH. Preferably, the temperature is 18-22° C. and the relative humidity is 30-50%.

In an embodiment the temperature is 5-30° C., such as 10-25° C., such as 10-30° C., such as 15-30° C. In another embodiment the relative humidity is 2-60% RH, such as 10-55% RH, such as 20-55% RH, such as 30-55% RH, such as 40-55% RH. Preferably the relative humidity is 30-50% RH.

According to a broad aspect of the invention, the result of the utilising the apparatus according to the present invention and the process according in their broadest aspects to the present invention is coiled collagen carrier with a number of windings, which coiled collagen carrier after being dried becomes form-stable. In the following, further characteristics of such a coiled collagen carrier are presented.

The windings being referred to as the outer windings are preferably each winding of the coiled collagen carrier except the inner most winding which typically is coiled to define an "S" when seen in a cross sectional view. In some embodiments the coiled collagen carrier may comprise only one outer winding and in such instances the winding being referred to as outer windings is preferably this single outer winding.

The coiled collagen carrier comprises a collagen layer. The collagen layer can be made from any suitable collagen, such as e.g. a collagen foam or sponge, such as e.g. the commercially available Nycomed "TachoTop" product. A preferred collagen type is equine collagen, such as e.g. native equine collagen extracted from sinews or human collagen, such as a solidified human collagen foam. The coiled collagen carrier also comprises a coating layer on top of the collagen layer, which comprises thrombin and fibrinogen. The thrombin is preferably mostly solid or solid. The fibrinogen is preferably mostly solid or solid. Preferably both the thrombin and fibrinogen are solid. Preferably the coating also comprises riboflavin, which provides a yellow colour and enables the medical practitioner to determine which side of the collagen carrier is the active side.

In preferred embodiments of the present invention, at least the outer windings or each winding of the coiled collagen carrier is orientated so that the coating layer constitutes the inner surface of each winding. In other embodiments of the present invention, each winding or at least the outer windings of the coiled collagen carrier is/are orientated so that the coating layer constitutes the outer surface of each of said windings.

In an embodiment of the present invention, the collagen carrier is preferably a layered construction, for example consisting of a layer of collagen and a coating layer on top of the collagen layer.

The coiled collagen carrier of the present invention is form-stable. This can for example mean that the coiled collagen carrier is form-stable in the sense that it does not un-coil "when at rest". In one embodiment of the present invention, the form-stability of the coiled collagen carrier diminishes when moisture is applied to it by which is meant that the product becomes more flexible (i.e. less form-stable). In a preferred embodiment of the present invention, the form-stability of the coiled collagen carrier is provided substantially only by the coating. At least some of the form-stability of the coiled collagen carrier can in one embodiment be provided by the outer most winding of the carrier. In one embodiment of the present invention, the form-stability of the coiled collagen carrier is provided by a region at the edge of the coiled collagen carrier adhering to the subjacent winding. In an embodiment of the present invention, the form-stability of the coiled collagen carrier is provided by the coiled collagen carrier having no mechanical tension. In an embodiment of the present invention, the form-stability of the coiled collagen carrier is provided by outbalancing mechanical tension acting to un-coil the coiled collagen carrier by an adherence between the windings. In an embodiment of the present invention, the form-stability of the coiled collagen carrier is provided by the coil having a elasticity module of 5-100 N/cm$^2$.

In one embodiment of the present invention, the form-stability is provided by the coiled collagen carrier forming a brittle coil which, when subjected to stress, breaks without significant deformation.

In a preferred embodiment of the present invention, the coiled collagen carrier in an unrolled configuration is a (preferably rectangular or square-shaped) sheet, preferably having a width, a length and a thickness. Preferably, said unrolled collagen carrier is a rectangular or square sheet. Preferably the sheet has a thickness of between 0.5 mm and 10 mm, such as e.g. 0.5-8 mm, for example 0.5-6 mm. In a preferred embodiment of the present invention, said thickness is preferably 1-4 mm. such as preferably 1-3 mm. The thickness can in one embodiment be at the most 4 mm, or at the most 5 mm, or at the most 6 mm, or at the most 7 mm. The unrolled collagen carrier preferably has a surface area on its top surface (which preferably is coated with the coated layer) of 4-100 cm$^2$, more preferably 5-75 cm$^2$, such as 10-50 cm², such as e.g. 20-30 cm², for example 25 cm² which can e.g. be given by a top surface of a 5 cm×5 cm square collagen sheet.

In an embodiment of the present invention, the coiled collagen carrier comprises or consists of three, four or five windings.

In an embodiment of the present invention, the coiled collagen carrier has a cylindrical shape with an outer diameter of less than 12 mm, such as less than 11 mm, such as less than 10 mm, such as less than 9 mm, such as less than 8 mm, such as less than 7 mm, such as less than 6 mm, such as less than 5 mm, such as less than 4 mm, such as less than 3 mm. For example, the coiled collagen carrier has an outer diameter of 1-12 mm, such as e.g. 3-11 mm, such as e.g. 5-10 mm, such as preferably 5-9 mm, such as e.g. 6-8 mm.

In an embodiment of the present invention, the coiled collagen carrier has an s-shaped inner most winding about the longitudinal axis of the coiled collagen carrier.

It is preferred that the coating of the coiled collagen carrier coating layer has no through-going cracks, such as through-going cracks visible by the naked eye.

The present invention further relates to a packed coiled collagen carrier, comprising the coiled collagen carrier according to the present invention arranged in a container. The container can for example be sealed to prevent contamination and/or degradation and/or to maintain form-stability of the coiled collagen carrier. Preferably the container is sealed to prevent contamination and/or absorption of liquid solvents such as e.g. water. The container can in one embodiment further comprise a desiccant, such as silica gel, arranged in the container.

The container can in an embodiment comprise an inner container and an outer container. Preferably, the inner container comprises a cavity shaped as a segment of a cylinder, and wherein the curved part of the cylinder segment extends at least 180°, the cavity being sealed by a tear-off or breakable foil. It is preferred that the outer container comprises a sealed pouch inside which the sealed inner container is arranged together with a desiccant.

The packed coiled collagen carrier according to the invention can also further comprise a label arranged to be visually inspected without opening the package and indicating whether the package with coiled collagen carrier has been exposed to radiation sterilization, such as to X-rays, such as to high-energy X-rays, or such as to gamma radiation, or such as to electron beams, or such as to ultraviolet light. The label can for example be arranged on the outside of the outer container.

The packed coiled collagen carrier according to the invention can also comprise a sterile plastic bag with a minimal amount of air inside, preferably with no air being in the bag, the bag being especially suited for protecting the coiled collagen carrier from being activated by bodily fluids when using it in e.g. surgery. This is illustrated in FIG. 10. This thin plastic bag may optionally be used after having unpacked the packed coiled collagen carrier according to the invention.

An embodiment of the invention relates to a process according to the invention, wherein ethanol is used for humidifying at least part of said collagen carrier.

An embodiment of the invention relates to a process according to the invention, wherein said ethanol is applied in an amount of about 0.8-10.4 mg/cm² of collagen carrier.

An embodiment of the invention relates to a process according to the invention, wherein said ethanol is applied in an amount of about 0.8-6.1 mg/cm² of said collagen carrier.

An embodiment of the invention relates to a process according to the invention, wherein said ethanol is applied in an amount of about 1.2-4.7 mg/cm² of said collagen carrier.

An embodiment of the invention relates to a process according to the invention, wherein said ethanol is applied to at least one side of said collagen carrier that does comprise said coating, e.g said ethanol is applied to at least one side of said collagen carrier, wherein said at least one side comprises a coating.

An embodiment of the invention relates to a process according to the invention, wherein said ethanol is applied to at least one side of said collagen carrier that does not comprise said coating.

An embodiment of the invention relates to a process according to the invention, wherein said ethanol is applied to at least two opposing sides of said collagen carrier wherein at least one of said sides comprises said coating.

An embodiment of the invention relates to a process according to the invention, wherein said coating is externally oriented upon said rolled compressed collagen carrier.

An embodiment of the invention relates to a process according to the invention, wherein said coating is internally oriented upon said rolled compressed collagen carrier.

An embodiment of the invention relates to a process according to the invention, wherein said compression is performed using roller compaction with a gap size between the rollers of no more than 1.0 mm, such as no more than 0.9 mm, preferably no more 0.75 mm and wherein the diameter of the rollers are about 10-100 mm. As outlined herein, the gap-size may be kept constant or be allowed to increase during compression. In embodiments where the gap-size increases during compression the above limits may be selected as the upper limits. In embodiments where the gap-size is kept constant, the above limits may be selected to be those limits.

An embodiment of the invention relates to a process according to the invention, wherein said sterilization is performed using gamma radiation.

An embodiment of the invention relates to a process according to the invention, wherein said collagen carriers are processed at 3-35° C. and 5-80% RH (relative humidity).

An embodiment of the invention relates to a process according to the invention, wherein said collagen carriers are processed at 18-22° C. and 36-65% RH (relative humidity).

An embodiment of the invention relates to a process according to the invention, wherein said drying results in said rolled compressed collagen carrier comprising no more than 2.0% w/w (residual) ethanol.

An embodiment of the invention relates to a process according to the invention, wherein said drying results in said rolled compressed collagen carrier having no more than 1.6% w/w (residual) ethanol.

An embodiment of the invention relates to a process according to the invention, wherein said drying results in said rolled compressed collagen carrier comprising no more than 10.0% w/w (residual) water.

An embodiment of the invention relates to a process according to the invention, wherein said drying results in said rolled compressed collagen carrier comprising no more than 8.0% w/w (residual) water.

An embodiment of the invention relates to a process according to the invention, wherein said coating comprises solid human fibrinogen in an amount of about 5.5 mg/cm² and solid human thrombin in an amount of about 2.0 IU/cm².

An embodiment of the invention relates to a process according to the invention, wherein said rolled compressed collagen carrier has a loss of coating immediately after un-rolling of less than 0.6 mg/cm² as measured by weighing.

An embodiment of the invention relates to a process according to the invention, wherein said rolled compressed collagen carrier is at least partly mechanically processed, thereby providing an at least partly mechanically rolled compressed collagen carrier, such as a mechanically rolled compressed collagen carrier.

An embodiment of the invention relates to a process according to the invention, wherein said collagen carrier has a density in the range of 3.0-4.5 mg/cm³. The density of a collagen carrier of the present invention is the density of the collagen carrier excluding the coating layer.

An embodiment of the invention relates to a process according to the invention, wherein said collagen carrier has a density in the range of 3.0-4.5 mg/cm³.

Please note that the density of a collagen carrier of the present invention is the density of the collagen carrier excluding the coating layer.

An embodiment of the invention relates to a process according to the invention, wherein said rolled compressed collagen carrier has a loss of coating immediately after un-rolling of less than 0.6 mg/cm² as measured by weighing.

It should be noted that embodiments and features described in the context of one of the aspects of the present invention also apply to the other aspects of the invention i.e. all aspects relating to a rolled compressed collagen carrier also apply to a compressed collagen carrier, or a rolled collagen carrier, or an unrolled rolled compressed collagen carrier.

All patent and non-patent references cited in the present application, are hereby incorporated by reference in their entirety.

The invention will now be described in further details in the following non-limiting examples.

BRIEF DESCRIPTION OF THE FIGURES

The present invention and in particular preferred embodiments thereof will now be disclosed in further details with reference to the accompanying figures. The figures show ways of implementing the present invention and are not to be construed as being limiting to other possible embodiments falling within the scope of the attached claim set.

DETAILED DESCRIPTION OF AN EMBODIMENT

Apparatus

Figure 1:
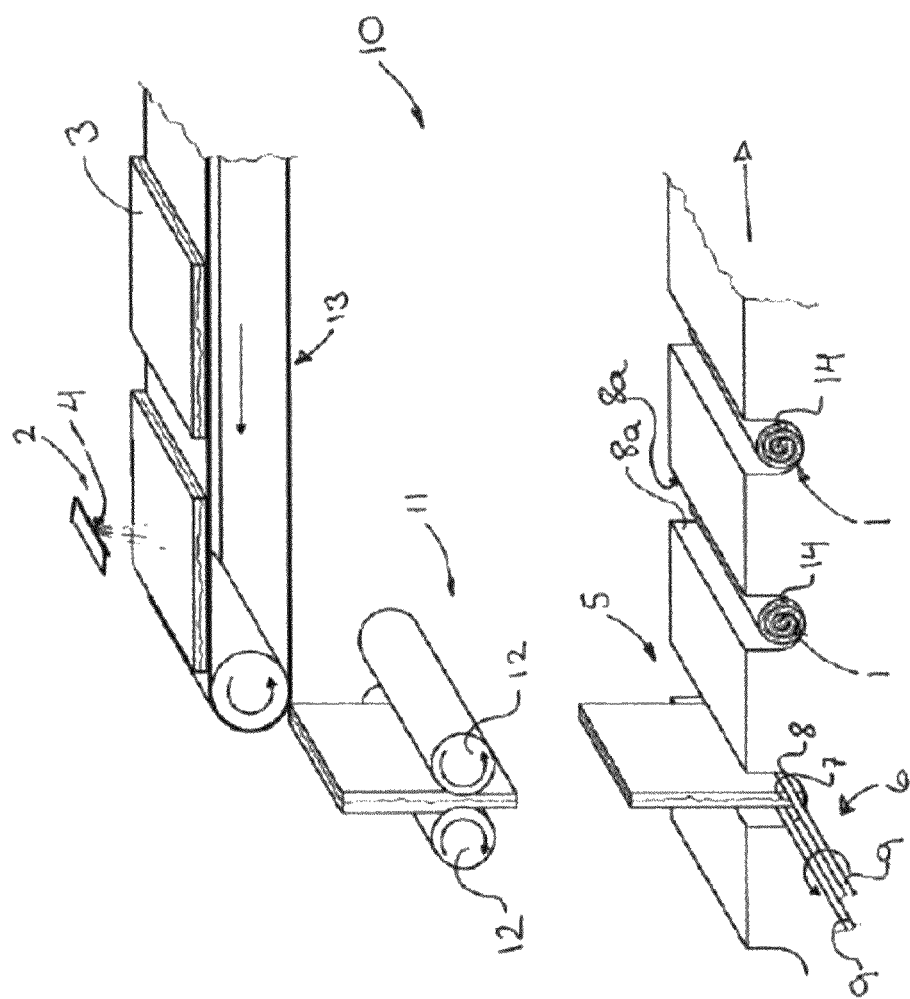
FIG. 1 discloses schematically a preferred embodiment of an apparatus for providing a coiled collagen carrier according to the present invention.

Reference is made to FIG. 1, which shows schematically a preferred embodiment of an apparatus 10 for providing a coiled collagen carrier. The apparatus comprises a number of elements as shown in the figure and comprises in particular a device for applying moisture 2 to a collagen carrier 3 prior to coiling of a collagen carrier as disclosed herein.

The device for applying moisture 2 comprises a spray nozzle 4 directed towards the surface of the coating layer of the collagen carrier, the spray nozzle 4 provides droplets as a mist or a spray of solvent. In the spray nozzle 4, droplets are produced assisted by sterile air, thereby ethanol is mixed with sterile air. Thus, the collagen carrier is orientated with its coating surface facing upwardly towards the spray nozzle 4. The solvent penetrates into the coating of the collagen carrier and softens the coating of the collagen carrier 3. It has been found that, it can be sufficient to humidify only the coating layer or an upper part thereof of the collagen carrier, although it is also possible to humidify the whole collagen carrier 3.

The apparatus 10 further comprises a coiling device 5, which is adapted to grip the moisturised collagen carrier 3 along an edge and coil it into a coiled collagen carrier 1. The coiling device 5 comprises rotatable gripping means 6 for gripping the collagen carrier along an edge 7 of the collagen carrier 3 and coil the collagen carrier 3 by rotation of the gripping means 6 around an axis being parallel to the longitudinal extension of the gripping means 6.

Gripping along the edge 7 and rotating the gripping means 6 allows coiling of the collagen carrier into a desired shape, preferably with the collagen carrier being supported during coiling. To assure coiling and assist in defining the shape of the coiled collagen carrier 1, the coiling device 5 further comprises a support device 8 supporting the collagen carrier while being coiled. The support device 8 is typically a cavity arranged relatively to the gripping means 6 so that the surface of the support device 8 acts as counter pressure means by at least a part of the collagen carrier 3 abutting at least a part of the inner surface of the cavity during coiling. As mentioned, the shape of the surface of the support device 8 at least assists in defining the shape of the coiled collagen carrier 1.

The gripping device 6 comprises a pair of elongated members 9, such as a pair of tweezers or pincers. The elongated members 9 has a longitudinal extension matching the width of the collagen carrier 1—the width of the collagen carrier is considered to be the dimension parallel to the extension of the elongated members 9—whereby the collagen carrier is gripped at the edge along the whole width by the elongated members 9.

Gripping of the collagen carrier 3 is accomplished by decreasing the distance between the two elongated members 9 once the collagen carrier 3 is located in between the elongated members 9 to an extent providing a gripping being sufficient to provide coiling once the elongated members 9 are rotated.

As shown in FIG. 1, the support device 8 is a cavity comprising a bottom part shaped as a segment of a cylinder having at least one open end through which the elongated members extend, and wherein the curved part of the cylinder segment extends at least 180°—in the embodiment shown in FIG. 1, the cylinder segments extends 180°. The upper part of the cavity is constituted by two parallel straight wall segments 8a so that the cavity has the shape of an open channel. The two wall segments 8a may alternatively be sloping slightly outwardly, such as in the order of 5°.

Thus, in the embodiment of FIG. 1, the cavity is channel-formed with two parallel side walls 8a extending from the bottom. This configuration of the cavity provides the channel with a generally "U"-shaped cross section, the bottom forming the curved part of the "U"-shaped cross-section and each side walls 8a forming the straight parts of the "U"-shaped cross section.

The elongated members 9 of the gripping device 6 extend into the cavity of the support device 8 through the open end. The elongated members 9 are furthermore extractable so that once the collagen carrier 3 has been coiled and is located in the cavity of the support device 8, the elongated members 9 are extracted from the coiled collagen carrier 1. The elongated members 9 are extracted in a direction being parallel to the longitudinal extension of members. When another collagen carrier 3 is to be coiled, the elongated members 9 are introduced back into the cavity of the support device 8 by moving the elongated members 9 in the opposite direction than during the extraction. Furthermore, the elongated members 9 are opened, that is the gap between the two members is larger than the thickness of a humidified and compressed collagen carrier 3 so that the elongate members 9 are ready to receive a collagen carrier in between them. By extractable is preferably meant that elongated members 9 can be removed from coiled collagen carrier after the coiling has been performed and in general also that they can be removed from the position where coiling is performed. Thus, the extractable is considered to cover also re-tractable.

Thus, the apparatus of FIG. 1 is adapted to move the pair of elongated members 9 in a reciprocating movement, so that the elongated members can be retracted after the collagen carrier has been coiled.

It is often found that the coiled collaged carrier stays inside the support device 8 while the elongated members 9 are extracted. However, if extraction of the elongate members 9 results in that the coiled collagen carrier moves out of the cavity with the elongate member 9, the apparatus may be fitted with a securing device e.g. limiting the size of the open end to a smaller dimension than the outer diameter of the coiled collagen carrier. This may be implemented by shaping the open end of the support device 8 with a small stop block in the form of an elevation at the open end of the support device 8, or shaping the open end of the support device having such limited size or an diaphragm, a slotted element or the like may be arranged to prevent the coiled element from be moved out of the support device while still allow extraction of the elongate members 9.

Thus, extraction of the elongated members 9 from the coiled collagen carrier 1 may involve securing of the coiled collagen carrier 1 inside the cavity if the elongated members 9 do not slide easily out from the coiled collagen carrier 1. Such securing may alternatively be provided by mechanically pressing the coiled collagen carrier toward the bottom of the cavity while extracting the elongated members, or a lattice structure may be arranged to prevent the coiled collagen member from sliding out of the cavity through the open end of the cavity while allowing extraction of the elongated members; thereby the dragging action from the elongated members on the coiled collagen carrier 1 may be outbalanced by the lattice structure, or the pressing action.

Once the collagen carrier has been coiled and the elongated members extracted, the elongate members may be used re-align the coiled collagen carrier in the support device 8 by pushing the coiled collagen carrier back into the centre of the support device, in cases where the extraction of the elongated members has shifted the position of the coiled collagen carrier towards the open end of the support device.

As indicated in FIG. 1, the result of the coiling is a coiled collagen carrier in the form of elongated member with an "S"-shaped core. The two curves of the "S" are defined by the elongated members 9. Furthermore, the rotation of the gripping device 6 is adapted to arrange the edge 14 so that it abuts the wall of the cavity when coiling is completed and the elongate members 9 are to be extracted. This means that the rotation of the elongate members is stopped when the entire collagen carrier 3 has been coiled and the 14 edge of the coiled collagen carrier 1 is orientated so that it abuts the wall of the support device 8. Thereby un-coiling after coiling may be prevented.

The apparatus 10 further comprises a compressing device 11. The compressing device 11 being arranged to compress the moisturised collagen carrier 3 prior to coiling of the moisturised collagen carrier, that is as indicated in FIG. 1, the compressing device being arranged after the device for applying moisture 2 and before the coiling device 5.

The compressing device comprises a pair of rollers 12 having a gap size being smaller than the thickness of the collagen carrier 3 before passing through the set of rollers 12 and being arranged to compress the moisturised collagen carrier 3 prior to coiling of the moisturised collagen carrier. The compression being provided because the gap in between the rollers is smaller than the thickness of the moisturised collagen carrier. As indicated in FIG. 1, the rollers 12 rotate in opposite directions so as to transport the collagen carrier through the pair of rollers 12 towards the coiling device 5.

The gap size between the rollers is selected so as to provide the desired compression ratio. Typically and preferred numbers for the gap size is no more than 0.5 mm, preferably no more than 0.6 mm or between 0.5-1.0 mm, or no more than 0.75 mm. However, the gap size should be selected in accordance with the thickness of the collagen carrier 3 so as to obtain the desired compression ratio.

The compression device may preferably include a certain flexibility allowing the compression ratio to be influenced by the collagen carrier and rendering the compression device more suited for handling collagen carriers of different densities. In the embodiments shown in FIG. 1 where the compression device comprises a set of rollers 12, this is implemented by allowing the rollers to move apart each so that the gap size increases. The movement of the rollers to increase the gap size is caused by the collagen carrier pressing on the surface of the rollers during its passage through the gap. Mechanically this is implemented by allowing some flexibility in the means used for mounting the rollers or by mounting one or both rollers 12 in a manner allowing displacement of the rollers in a direction being perpendicular to the axis of rotation and biasing the rollers towards each other by springs.

Figure 2:
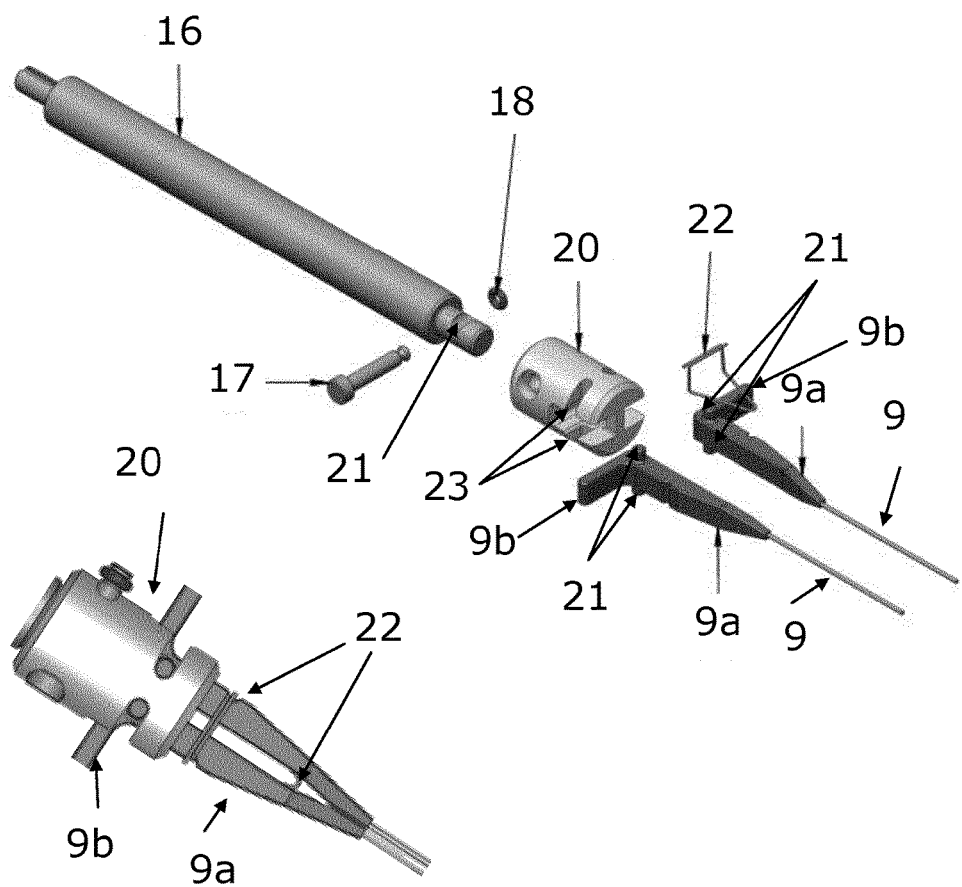
FIG. 2 shows the rotatable gripping means for gripping the collagen carrier along an edge and coiling the collagen carrier together with some of its element for providing the gripping and the rotation; in the upper part of FIG. 2 the gripping means is shown in an exploded view and in the lower part of FIG. 2, a section of the gripping means is shown in assembled state.

FIG. 2 shows the rotatable gripping means for gripping the collagen carrier along an edge and coiling the collagen carrier together with some of its element for providing the gripping and the rotation; in the upper part of FIG. 2 the gripping means is shown in an exploded view and in the lower part of FIG. 2, a section of the gripping means is shown in assembled state. The gripping means comprises a pair of tweezers or pincers forming the elongated members 9. These elongated members have at one end an L-shape element 9a, 9b. In the corners of the L-shaped elements pivoting studs 21 is provided which fit into corresponding pivoting openings 23 of the assembling element 20. When the L-shaped elements 9a, 9b are arranged in the assembling element 20, the shorter legs 9b of the L-shape elements protrudes out from the assembling element 20 in a direction being perpendicular to the longitudinal direction of the shaft 16. The longer legs 9a protrude also from the assembling element but in direction being aligned with the longitudinal direction of the shaft 16.

The gripping movement of the elongated members 9 are provided by applying a force to the protruding parts 9b of the L-shaped elements which will cause the L-shaped elements to pivot around the pivoting studs 21 whereby the elongated members 9 will move towards each other. Movement of the elongated member 9 to provide release is provided by moving the protruding parts of the L-shaped elements in opposite directing, that is pivoting the L-shaped elements in opposite direction than to accomplish the gripping.

To assist gripping, a spring 22 is applied to the L-shaped elements as shown in the lower part of FIG. 2, which springs are pre-tensioned to keep the elongated members 9 biased towards each other (in a gripping position). It is noted that the spring 22 at the upper part is constituted by two parallel extending pins so (see e.g. the lower part of FIG. 2) so that the spring acts as a clamp spring. The assembling element 22 is mounted on a shaft 16 by use of a pin bolt 17 which penetrates through the assembling element 20 and fits into a recess 24 provided in the part of the shaft 16 protruding into the assembling element 20. The pin bolt is fixated by use of a lock ring 18. The recess 24 is provided off-centre of the shaft 16. The shaft 16 is arranged in a device which rotates the shaft and provides a reciprocating movement of the shaft 16, and as the assembling element 22 is fixed relatively to the shaft 16 a reciprocating movement and rotation of the shaft results in that the elongated members 9 also performs these movements.

The rotation of the shaft 16 is preferably performed by use of a stepper motor so that the angular position of the shaft is well-defined and thereby also the number of revolutions performed.

After the collagen carrier 3 has been coiled into a coiled collagen carrier it is still moisturised (contains solvent) and is still softened. To provide a form-stable coiled collagen carrier 1, the collagen carrier is de-moisturised which is provided by drying the coiled collagen carrier 1. The apparatus accordingly further comprising at least a drying means (not shown in the figure) for drying one or more coiled collagen carriers subsequently to the coiling.

The drying means may typically be embodied as a drying tunnel through which the coiled collagen carrier 1 passes and inside which drying tunnel the temperature is elevated relatively to the temperature of the coiled collagen carrier 1 and the relative solvent content in the air is kept low. These two measures (elevated temperature and low relative solvent content) promote transport of solvent from the coiled collagen carrier 1 to the air inside the drying tunnel. Forced circulation of the air may advantageously be applied to enhance removal of solvent from the coiled collagen carrier 1.

The drying means comprises a pump (not shown in FIG. 1) sucking or blowing air, preferably being sterile filtered. It is noted, that the main purpose of the drying means is to remove excess solvent applied in during the moisturizing of the collagen carrier and that this solvent is different from water.

The apparatus may comprise means for applying heat inside the drying tunnel. However, in the cases that the solvent used is highly flammable (e.g. ethanol and/or isopropanol) care should be taken to avoid explosion and/or fire which could be introduced by such heating means.

The direction of the air being sucked or blown though the drying tunnel is typically either counter current to the conveying direction of the coiled collagen carriers or is in the same direction as the conveying direction of the coiled collagen carriers.

In a preferred embodiment of the apparatus, the purpose of the drying tunnel is to reduce the Ethanol content in the coiled collagen carrier.

After the coiled collagen carriers has been dried in e.g. the drying tunnel for preferably about 30 minutes, the coiled collagen carriers may be further dried e.g. by arranging the coiled collagen carriers in a sealed box together with a desiccant. The coiled collagen carriers are preferably present in the sealed box for up to 72 hours.

The water content, if present, is reduced at a later time point when the coiled collagen carrier is placed in a container over a desiccant and arranged in an outer container.

Preferably, the air is sucked into the drying tunnel form the ends by a centrally placed fan above the machine—counter current to the direction in which the fleeces are being moved (this is preferred to minimize the risk of explosions outside of the drying tunnel). For the drying phases for reduction of Ethanol, the preferred requirement is to have the humidity of the air inside the drying tunnel as the same as the overall requirements for the humidity in the room in which the machine is placed that is typically 30-50% RH and 18-22° C.

The apparatus is advantageously embodied so as to provide an automated production of coiled collagen carriers 1. As indicated in FIG. 1, the apparatus is embodied as an assembly line which conveys the collagen carriers 3 through the various production stages.

Thus, apparatus 10 comprises a first conveyer device 13 which conveys collagen carriers 3 prior to coiling past the moisturiser device 2 and to the coiling device 5.

On its way from the moisture device 2 and to the coiling device 5, the moisturised collagen carriers 3 pass through the pair of rollers 12 arranged to compress the moisturised collagen carrier prior to coiling of the moisturised collagen carrier, and the first conveyer device 13 conveys the moisturised collagen carriers 3 to the pair of rollers 12. It is noted that conveying of the moisturised collagen carrier 3 from the end of the first conveyer device 13 and to the gap between the pair of rollers 12 can be assisted by guides (see FIG. 3) which guide the moisturised collagen carriers 3 to the pair of rollers 12. As a compression is performed by the pair of rollers 12, the rotation of the rollers 12 conveys the moisturised collagen carrier 3 through the compression device 11 and to the coiling device 5. Again, suitable guiding means (see FIG. 3) may be applied to guide the collagen carriers 3 to the position in the cavity of the coiling device 5 in which the gripping means 6 may grip the collagen carrier along an edge and coil the collagen carrier 3. The guides and guiding means are made from an inert material that does not contaminate the collagen carriers by e.g. rubbing off of material.

Although the first conveyer device 13 is shown as a single conveyer 13 belt, the first conveyer device preferably comprises two conveying elements, preferably in the form of two separate conveyer belts. One of these conveying elements (first conveying element) is used for conveying the collagen carrier towards the moisturiser device 2 and a subsequent conveying element (second conveying element) for conveying the collagen carrier past the moisturiser device 2 and to a guiding means (see FIG. 3) and thereby to the pair of rollers 12. The two conveying elements are controlled so that a collagen carrier which has not yet been moisturised is only conveyed to the second conveying element that conveys it past the moisturiser device in situations where the compression device 11 and the coiling device 5 is ready to receive a moisturised collagen carrier; that is in situations where the compression device 11 and the coiling device 5 are not compressing or coiling another moisturised collagen carrier. This has inter alia the advantage that the moisturised collagen carrier does not go through any unnecessary waiting time which could result in evaporation of solvent and/or undesirable changes of the moisturised collaged carrier due to be moisturised.

Figure 3:
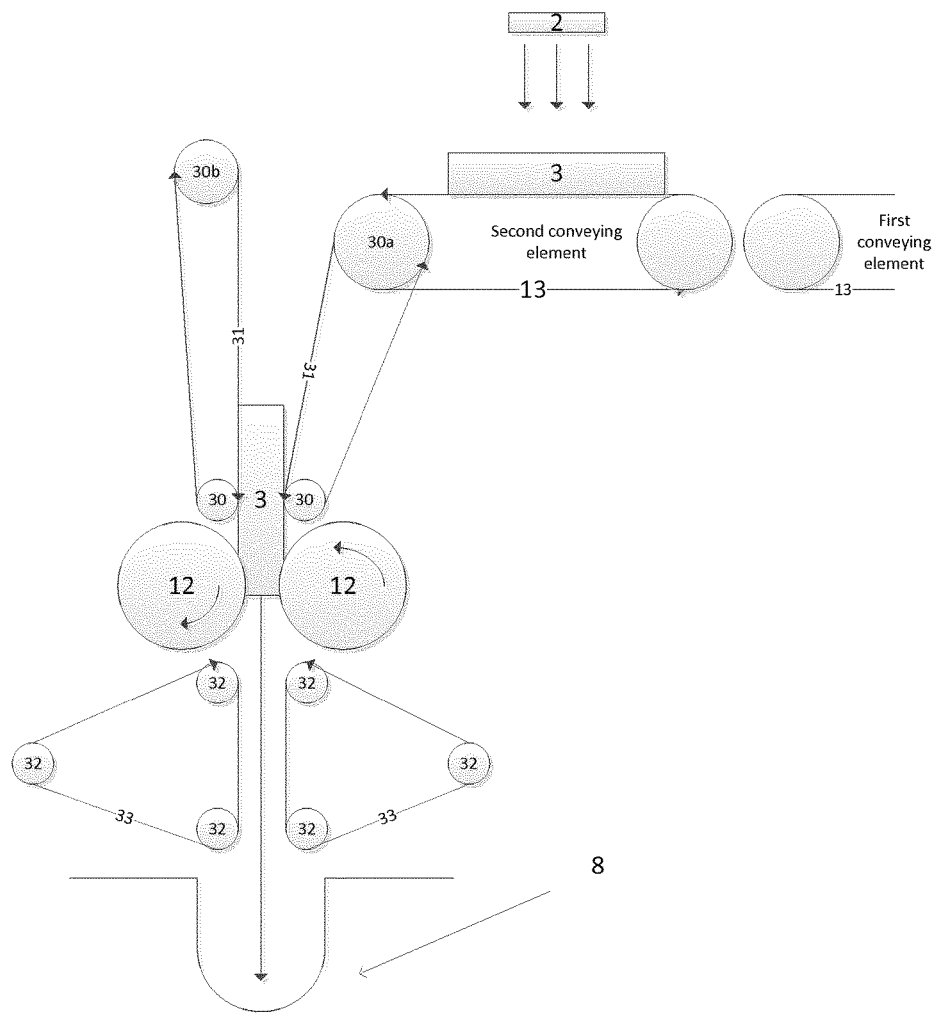
FIG. 3 shows schematically guiding means for guiding a humidified collagen carrier through a pair of rollers and to a support device, FIGS. 4a and b each shows details of a preferred embodiment of an apparatus according to the present invention in a 3-dimensional view.

The guiding means for guiding the moisturised collagen carrier 3 to the pair of roller 12 and for guiding the compressed and moisturised collagen carrier 3 to the coiling device 5 is shown schematically in FIG. 3. The guiding also conveys the collagen carrier. The guiding means comprises an upper guiding part 30, 31 and a lower guiding part 32, 33.

The upper guiding part comprises two sets of wheels 30, 30a and 30, 30b and conveyer belts arranged on the wheel pairs in the form of rubber bands 31 with a circular cross sections. The wheel 30a forms part of the first conveyer element of the first conveyer device 13 and rotates along with the movement of the second conveyer element. The wheel 30 rotates in a manner so that the speed of the conveyer belts 31 in between which the moisturised collagen carrier is present after moisturising is equal. As also shown in FIG. 3, the upper guiding part forms a funnel shape passage tapering towards the pair of rollers 12. The speed of the conveyer belts 31 is furthermore equal to the angular velocity of the rollers 12. The reason for equalising the speed of the moving elements of guiding means and the rollers is to avoid shearing forces to be applied to the surface of the collagen carrier.

The lower guiding part comprises two set of wheels each set comprising three wheels in a double triangular configuration as depicted in FIG. 3. The conveyer belts 33 in the form of rubber bands are arranged on the wheels 32. The conveyer belts 33 are moved by one of the wheels of each pair is actively rotated while the remaining two wheels are free-wheeling. The conveyer belts 33 thereby defines a passage below the gap between the pair of roller 12 into which the collagen carrier proceeds after being compressed.

In both the upper and lower guiding parts, the conveyer belts 31 and 32 are each constituted by two parallel rubber bands distanced apart with a distance being smaller than the width of the collagen carrier so as to increase the support of the collagen carrier while being conveyed.

Due to the definition of the passages above and below the pair of rollers, the path the collagen carrier may follow is spatially restricted by the conveyer belts 31, 33.

Furthermore, to assist the automated production of coiled collagen carriers 1, the cavity of the coiling device 5 is formed in a second conveyer device. While the first conveyer device 13 conveys the collagen carrier 3 at a constant speed, the second conveyer device typically conveys coiled collagen carriers 1 step wise; that is as long as the coiling takes place, the second conveyer device is at rest and once coiling is finished (the edge 14 is arranged so as to abut the surface of cavity and the elongated members 9 extracted) the second conveyer device moves to arrange an empty cavity below the pair of rollers and in front of the extracted elongated members 9.

The conveying speed of the first conveyer device is set in accordance with the amount of solvent being applied from the nozzles 14 to obtain a predefined amount solvent applied per surface area of the collagen carrier 3.

In many of the preferred embodiments, the cavity is formed in a tray having a plurality of cavities and said tray being arranged on and conveyed by a second conveyer device of the apparatus. Thus, the formulation "the cavity of the coiling device 5 is formed in a second conveyer device" includes embodiments where the cavities are provided directly in e.g. a conveyer belt and where the cavities are provided in a tray.

Such trays, which generally are preferred, are arranged on a conveyer belt in a manner where the position of the trays relatively to the conveyer is known and fixed. Typically, the conveyer belt conveyer belt has teeth which co-operates with indentations or notches in the tray so that the tray is moved along with the conveyer belt in a mutually fixed position.

The trays are often made stackable so that they can be stacked while containing coiled collagen carriers in the cavities without the coiled collagen carrier being abutted by e.g. tray arranged above in a stack. This is often accomplished by making the cavities deeper than the diameter of the coiled collagen carrier and longer than the length of the coiled collagen carrier.

It is often preferred to use disposable trays and such disposable trays are often made from plastic, such as PET, and produced by moulding. However, the tray may also be made of metal in which case, they may be reused by cleaning and sterilization e.g. by use of an autoclave.

The orientations and mutual arrangements of the various parts presented in FIG. 1 are implemented in the apparatus as implemented in the figure. That is, the first conveyer device 13 is arranged above the coiling device 5 with the pair of rollers 12 arranged in between.

Explosion or risk of fire may be a critical issue to consider as the collagen carrier is humidified with a flammable solvent such as ethanol and/or isopropanol Furthermore, contamination of the collagen carriers may often an issue that must be taken care of during humidification, compression, coiling and drying. Mainly to limit the explosion risk and/or risk of fire and to some extend also to avoid contamination, the various parts used for producing the coiled collagen carrier are shielded from the environment by a cabinet. Thus, the apparatus may typically comprise a cabinet sealing the moisturiser device 2, and/or the pair of rollers 12, and/or the coiling device 5, and/or the support device 8, and/or the first 13 and/or the second conveyer device.

As the solvent in some instances is highly flammable, the apparatus may advantageously comprise suction means for sucking out gas and/or droplets originating from the humidification as well as a closed cabinet with a defined socall ATEX zone.

After the collagen carrier 3 has been coiled they are still present in the cavities of the support device. The coiled collagen carriers 3 are to be packed in a suitable package and the apparatus comprising a device for conveying a coiled collagen carrier from the supporting device and arranging it in a container forming the packaging for the coiled collagen carrier.

Prior to packaging the coiled collagen carrier 3 in suitable package, the collagen carriers are further dried to further dry off solvent and water (if present). This is done by arranging the collagen carriers 3 in suitable sealed containers together with a desiccant and leave them at rest for 72 hours. The desiccant will during that period absorb further solvent and water.

The packaging for the coiled collagen carrier comprises in many preferred embodiments two containers and a desiccant. The two containers are an outer container and inner container. The inner container contains the coiled collaged carrier and is arranged together with a desiccant inside the outer container.

The inner container has a compartment with an opening, inside which compartment the coiled collagen carrier is arranged manually. However, the arrangement may be carried out by a robot which grasps a coiled collagen carrier located in a cavity of the support device and moves it into the compartment of the inner container through the opening.

The apparatus typically has a cover arranging device, in the form of robot, which arranges a cover to at least cover the opening of the inner container. The apparatus has a welding or gluing device to facility attachment of the cover to the inner container.

The material of the cover attached to the inner container is permeable to gas and/or liquid and once the coiled collagen carrier is arranged in the inner container and the cover attached, the inner container may be arranged in the outer container.

To accomplish the transfer of the inner container to outer container, the apparatus may have a device arranging the inner container in the outer container. This device is typically in the form of a robot. The outer container is made from a non-permeable material and closed in a sealed manner. The closing of the outer container is provided by a heat welding device or a gluing device closing the outer container by heat welding or gluing.

As the outer container is closed in a sealed manner and the coiled collagen carrier may still container some solvent and/or water, a desiccant is arranged inside the outer container and outside the inner container as disclosed above. The main purpose of the desiccant is to take up water absorbed by th coiled collagen carrier during packaging but may also absorb water permeating through the cover applied to the inner container and/or water being trapped inside the outer container in general. The desiccant is arranged by a device designed for this purpose.

As disclosed above, the apparatus may have devices for conveying and/or arranging the coiled collagen carrier, the cover, the desiccant and/or the inner container. These devices are preferably robots such as a numerically controlled robot arm with gripping means. The gripping means may be robot claws, sucking disc and the like.

The automated handling of the coiled collagen carrier to arrange the pack the coiled collagen carrier may be replaced by a manual handling. However, in order to maintain a sufficient production speed, unified quality and avoid contamination the automated handling is often preferred.

Although great care is taken during in the process of coiling and packing, there might still be a risk that the packed coiled collagen carrier may be contaminated with e.g. germ. The apparatus may accordingly further comprise a sterilizing device arranged to sterilize the packed coiled collagen carrier. Such a sterilizing device is typically embodied as a source of radio magnetic radiation adapted to radiate the electromagnetic radiation towards and through the packed coiled collagen carrier, that is towards and through the outer container, the desiccant, the cover, the coiled collagen carrier and the coiled collagen carrier. Alternatively, the sterilizing may be performed remote from the apparatus, e.g. by shipping the collagen carriers either being packed or not packed to a sterilization department remote from the production site for coiled collagen carriers.

As the quality of the coiled collagen carrier often has to fulfil certain prescribed criteria the apparatus may comprises elements that monitor e.g.

- the physical appearance of the coiled collagen carrier (lack of e.g. coating is often visually identifiable),
- whether a coiled collagen carrier is present in the inner container before a cover is attached,
- whether a desiccant is present in the outer container before the inner container is arranged therein and the outer container is closed,
- whether production details such as batch number, production date etc is printed on certain parts of the container(s),
- whether the packed coiled collagen carrier has been sterilized.

Such elements for monitoring may be image recognition devices adapted to image the processing of the apparatus at preselected stages, examine the images and signal a discard signal for a coiled collagen carrier in case the examining reveals that a coiled collagen carrier falls outside quality ranges. For instance, if the image recognition device detects that no coiled collagen carrier is present in the compartment of the inner container, the device sends a discard signal to an supervising computer which in turn activates a discard of the inner container so as to avoid further handling of that particular inner container (as this would otherwise result in that the final closed outer container would not contain any coiled collagen carrier).

As disclosed above, it is often desirable to control the atmosphere surrounding the collagen carrier during forming it into a coiled collagen carrier and during packaging. In order to accomplish that, the apparatus may be equipped with air-conditioning devices maintaining the atmosphere surrounding the collagen carrier and humidification device at least while being humidified, compressed and coiled at a temperature of 18-22° C. and a relative humidity of 30-50%.

Reference is made to FIG. 4 which shows schematically how a production facility according to the present invention may be divided into a primary production room and a secondary production room. The primary production room contains the operation necessary to provide produce a coiled collaged collagen carrier from a collagen carrier and arranged the coiled collagen carrier in an inner container with a cover. As the collagen carrier in the primary production room is unprotected from e.g. contamination until it is arranged in the inner container and a cover is arranged to the inner container, the demands to sterility etc in the primary production room are high.

It should be noted that although the cover applied to the inner container constitutes some kind of barrier, the cover is made from a permeable material that does not provides a barrier through which contamination may not pass through. However, once the coiled collagen carrier is arranged in the inner container and the cover applied, the risk of contamination and cross contamination in between coiled collagen carriers is lowered. Furthermore, as each handling of the coiled collagen carrier may represent a risk of contamination, it is desirable to divide the production facilities into separate rooms.

Accordingly, the elements of the apparatus according to the present invention taking part in providing a coiled collagen carrier and arranging the coiled collagen carrier in an inner container with a cover are arranged in a primary production room being sealed by airlocks.

Furthermore, the elements of the apparatus taking part in arranging the inner container and desiccant in a second outer container, sealing the outer container and sterilising the packed coiled collagen carrier are arranged in a secondary production room sealed by airlocks.

In the embodiment shown in FIG. 4, the primary and secondary production rooms are connected by a conveyer extending in between the two production rooms and comprising an airlock whereby the inner container being conveyed by the conveyer from the primary production room to the secondary production room.

FIG. 4 shows details of a preferred embodiment of an apparatus according to the present invention in a 3-dimensional view. The same numerals as used in relation to FIGS. 1-3 are also used in FIG. 4. As shown in figure, the first conveyer device 13 comprises a first conveyer element 13a and a second conveyer element 13b. The moisturising device 2 is encircled by a line labelled 2 above the second conveyer element 13b.

The guiding means for guiding the moisturised collagen carrier 3 (not shown) to the pair of roller 12 and for guiding the compressed and moisturised collagen carrier 3 to the coiling device 5 is above the support device 8. In the embodiment shown in FIG. 4, the support device 8 is a separate element, a tray, comprising sixteen cavities, and the support device 8 is arranged on and conveyed by a second conveyer device 34 (the arrows along the conveyer belt of the second conveyer device 34 indicates the direction of the movement of the belt).

As also shown in FIG. 4, the second conveyer device extends into a drying tunnel 35 (as disclosed herein). Air is sucked or blown into the drying channel through an opening (not shown) arranged midway downstream of the drying tunnel and the air escapes (when blowing) or enters (when sucking) through the opens ends of the drying tunnel. A further tunnel is arranged in the region of the opening inside the drying tunnel, through which further tunnel the support device pass. The purpose of the further tunnel is to hinder air being blown out of or suck into the drying tunnel 35 flom blowing the coiled collagen carriers out of the support device 8. The further tunnel acts as an air distributer which distributes the air flow along the space defined by the outer surface of the further tunnel and in the inner side of the drying tunnel 35.

A trough 36 with suction is applied below the coiling device 5 to ventilate the apparatus at least in the region of the coiling device.

As shown, the guiding means comprises an upper guiding part 30, 31 and a lower guiding part 32, 33. The upper guiding part comprises two sets of wheels 30, 30a and 30, 30b and conveyer belts arranged on the wheel pairs in the form of rubber bands 31 with a circular cross sections. The wheel 30a forms part of the first conveyer element of the first conveyer device 13 and rotates along with the movement of the second conveyer element. The wheel 30 rotates in a manner so that the speed of the conveyer belts 31 in between which the moisturised collagen carrier is present after moisturising is equal. As also shown in FIG. 4, the upper guiding part forms a funnel shape passage tapering towards the pair of rollers 12. The speed of the conveyer belts 31 is furthermore equal to the angular velocity of the rollers 12. The reason for equalising the speed of the moving elements of guiding means and the rollers is to avoid shearing forces to be applied to the surface of the collagen carrier.

The lower guiding part comprises two set of wheels each set comprising three wheels in a double triangular configuration as depicted in FIG. 3. The conveyer belts 33 in the form of rubber bands are arranged on the wheels 32. The conveyer belts 33 are moved by one of the wheels of each pair is actively rotated while the remaining two wheels are free-wheeling. The conveyer belts 33 thereby define a passage below the gap between the pair of roller 12 into which the collagen carrier proceeds after being compressed.

In both the upper and lower guiding parts, the conveyer belts 31 and 32 are each constituted by two parallel rubber bands distanced apart with a distance being smaller than the width of the collagen carrier so as to increase the support of the collagen carrier while being conveyed.

Figure 4A:
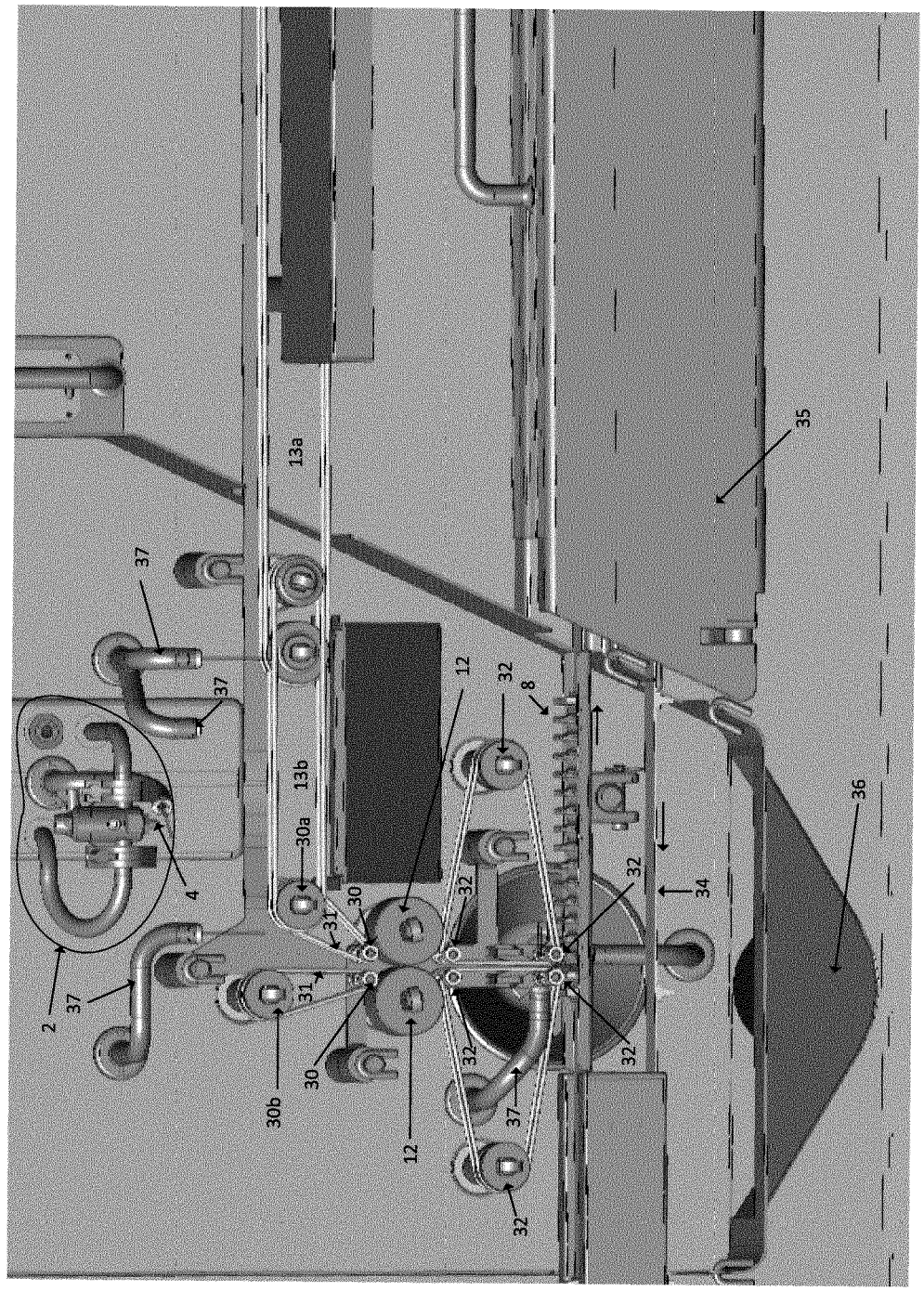
FIG. 4b shows a close up of in particular the coiling device 5 shown in FIG. 4a, FIG. 5 discloses schematically a preferred layout of production facility according to the present invention.
Figure 4B:
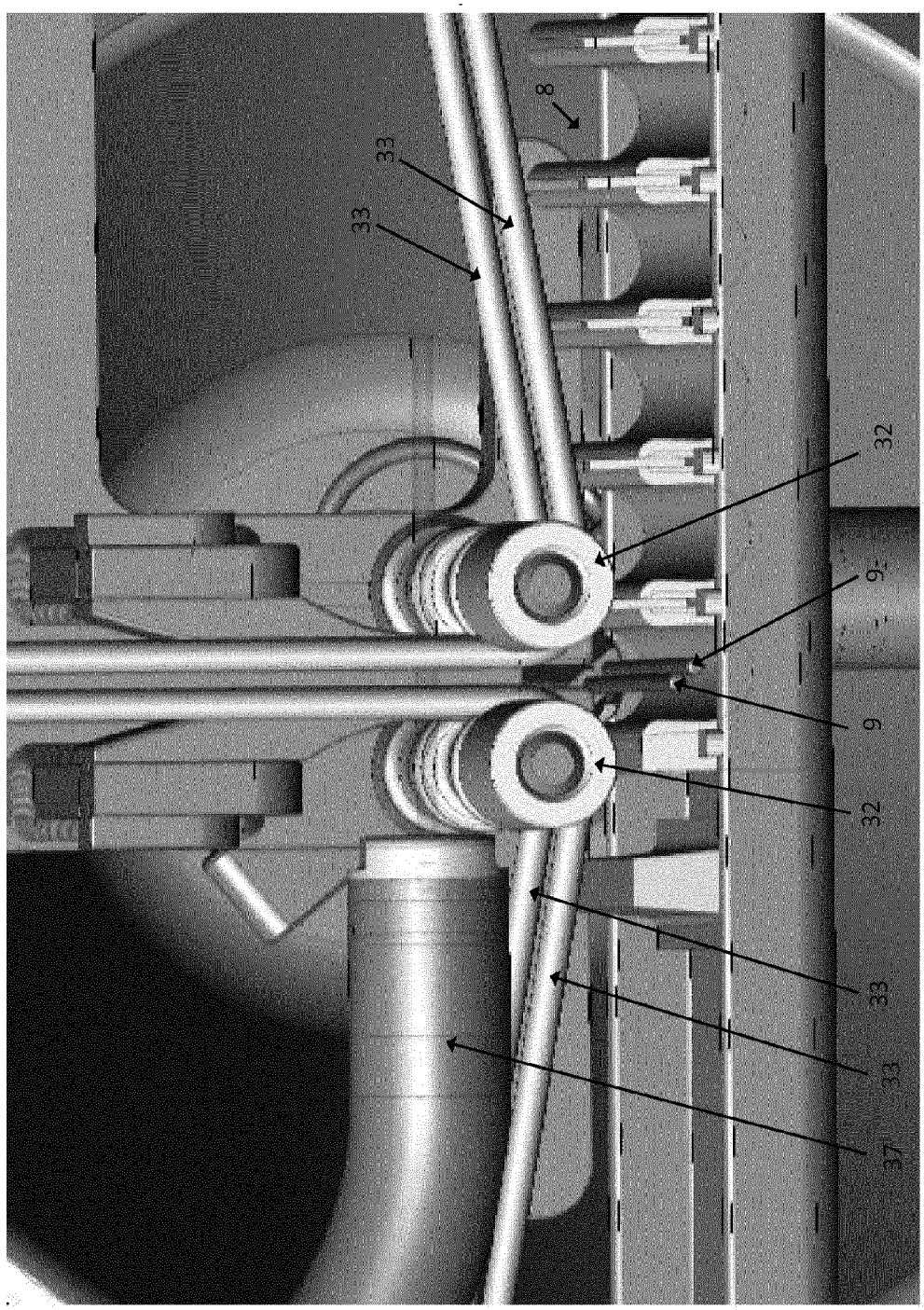

FIG. 4b shows a close up of in particular the coiling device 5 shown in FIG. 4a

The elements in FIG. 4 labelled 37 are sensors, typically being optical sensors and the line of sight being indicated, arranged to monitor the various steps performed by the apparatus.

Processes

The apparatuses disclosed herein are adapted to perform a process for coiling a collagen carrier comprising a collagen layer and a coating layer comprising mostly solid fibrinogen and mostly solid thrombin. In the following, preferred embodiments of processes according to the present invention will be disclosed. Reference is made to FIG. 1 and the elements and parts presented therein are referenced by reference numbers—this is not intended to limit the processes to the apparatus disclosed in FIGS. 1, 2, 3 and 4.

Processes according to the invention typically comprise the sequential steps of humidifying at least part of a collagen carrier 3, and coiling the collagen carrier 3 by gripping the collagen carrier 3 between a pair of elongated members 9, and rotating the pair of elongated members 9 about an axis being parallel to a longitudinal extension of the elongated members 9 in order to coil the collagen carrier 3 on the members, while the collagen carrier 3 is supported by a support device 8.

The humidifying and coiling steps are preferably executed as two separate steps as disclosed above in relation to the embodiment of the apparatus 10, which steps are executed consecutively to each other. The time between humidifying and coiling is selected so that the softening effect obtained by the humidification on the collagen carrier 3 is present while the collagen carrier 3 is coiled.

After the collagen carrier 3 has been coiled, the process involves a step of drying the coiled collagen carrier 1. The drying steps removes solvent from the coiled collagen carrier and the drying step is typically and preferably performed while the coiled collagen carrier is supported so as to maintain its coiled shape during drying. The result of the process is a form-stable coiled collagen carrier 1.

The coiling is performed by gripping the collagen carrier using at least one gripping device and the collagen carrier is gripped along an edge of the collagen carrier 3. The coiling is performed by gripping the collagen carrier using at least one pair of tweezers or pincers 9.

Drying of the coiled collagen carrier 1 is typically performed by blowing air with humidity lower than the coiled collagen carrier and optionally applying heat to the air to enhance e.g. evaporation of the liquid used to humidify the collagen carrier 3. It is noted that the term humidity is to be understood broadly and not limited only to water. For instance, humidity is also used to cover the concentration in the air of the solvent used to humidify the collagen carrier 3.

As noted above, the process involves humidifying at least a part of the collagen carrier and in some embodiments of the invention the part being humidified is the coating layer. Typically, the humidification step is performed by spraying droplet of liquid onto the surface of the coating layer, and the humidification is obtained by the liquid penetrating into the coating layer of the collagen carrier 3 e.g. by a capillary action. Thus, the amount of liquid present in e.g. the coating layer may vary with the depth; however, as one aim of humidifying is to soften the collagen carrier 3 such variations in liquid amounts are acceptable. In many preferred embodiment, the coating layer has been humidified using a solvent applied onto the surface of the coating layer in an amount 1.2-10.75 mg/cm$^2$ surface of collagen carrier 3. The solvent used typically comprises or consists of ethanol.

A process according to the present invention may further comprise a step of compressing the collagen carrier 3 which compression reduces the thickness of the collagen carrier. While different compression ratio, i.e. ratio between the thickness of the collagen carrier 3 before and after compression, may vary, the collagen carrier is preferably compressed with a compression ratio between 6 and 12. The compression is performed after the humidifying step and before the coiling step, that is the compression is performed prior to coiling of the collagen carrier.

An efficient compression has proven to be performed by passing the humidified collagen carrier through a set of rollers 12 having a gap size being smaller than the thickness of the collagen carrier 3 before passing through the set of rollers 12. The gap size is selected so as to provide the desired compression ratio. Typically and preferred numbers for the gap size is no more than 0.5 mm, preferably no more than 0.6 mm or between 0.5-1.0 mm, or no more than 0.75 mm. However, the gap size should be selected in accordance with the thickness of the collagen carrier 3 so as to obtain the desired compression ratio.

After the collagen carrier 3 has been humidified, optionally compressed and coiled, the coiled collagen carrier 1 is still softened and may have a tendency to un-coil during drying e.g. due to gravity effects and/or some mechanical tension in coiled collagen carrier 1. To assure that the coiled collagen carrier 1 hardens in the coiled shape, the edge (see number 14 in FIG. 1) of the coiled collagen carrier 1 arranged on the outside of the coil after coiling is abutting the surface of the cavity and thereby being fixated by the support device 8 relatively to the coiled collagen carrier 1 during drying. It is noted that fixated refers to that the coiled collagen carrier 1 being orientated in a pre-defined orientation relatively to the support device and that preferably no further means, such as straps, pressing means or the like, are applied to fixate the coiled collagen carrier Once the coiled collagen carrier 1 has dried the softened parts of the collagen carrier has hardened and the coiled collagen carrier 1 is form-stable. The collagen carrier is typically said have been dried when is have passed through the drying tunnel and have been arranged in a sealed container for about 72 hours together with a desiccant.

The support device 8 is as disclosed above with reference to FIG. 1 a cavity having a bottom part shaped as a segment of a cylinder having at least one open end through which the elongated members extend into the cavity, and wherein the curved part of the cylinder segment extends at least 180°. During the coiling process, the outer edge 14 of the collagen carrier is arranged inside the part of the cavity formed as a segment of cylinder and the edge 14 abuts the inner surface of the cavity. Once the edge 14 abuts the inner surface, the coiling process is terminated and the gripping means in the form of a pair of elongated members 9 is extracted from the coiled collagen carrier through the open end of the cavity.

Prior to coiling, the elongated members 9 are positioned in the cavity in the support device in a predefined position where the elongated members are ready to receive a collagen carrier. Furthermore, the elongated members 9 are opened in the sense that the gap between the elongated members 9 is larger than the thickness of a humidified and compressed collagen carrier.

Extraction of the elongated members 9 from the coiled collagen carrier 1 may involve securing of the coiled collagen carrier 1 inside the cavity if the elongated members 9 do not slide easily out from the coiled collagen carrier 1. Such securing may be provided by the means disclosed above in relation to the apparatus shown in FIG. 1

Once the elongated members 9 are extracted, any securing may be released. The extraction of the elongated members 9 is typically performed before drying of the coiled collagen carrier. The pair of elongated members may be constituted by a pair of tweezers and the process disclosed above is the same.

The atmosphere surrounding the collagen carrier 3 and humidification device 2 while the collagen carrier 3 being humidified, compressed and coiled is typically maintained at a temperature of 18-22° C. and a relative humidity of 30-50%. After the coiled collagen carrier 1 has been dried to form a form-stable collagen carrier, the process may include the step of arranging the form-stable coiled collagen carrier 1 in a container and subsequently sealing the container. The step of arranging the coiled collagen carrier in a sealed container prevents the coiled collagen carrier 1 from being humidified and/or contaminated. Furthermore, the step of arranging the coiled collagen carrier 1 in a sealed container may also comprise the steps of arranging the coiled collagen carrier 1 in an inner container and arranging the inner container in an outer container. In addition, a desiccator may be arranged inside the outer container prior to sealing of the container.

While an aim of the process is to provide a sterile coiled collagen carrier packed in one or more containers, the process may also include a sterilizing step during which the container(s) with coiled collagen carrier is exposed to a sterilizing process. The sterilizing may typically be radiation sterilization. To make it easy detectable whether a given coiled collagen carrier 1 has been sterilized, a label indicating whether sterilization has been carried out or not may be arranged on the outside of the outer container—or container in general.

An often preferred sterilization step comprises sterilizing the coiled collagen carrier 1 using gamma radiation. The sterilization of the coiled collagen carrier 1 is often performed to a sterility assurance level (SAL) of $10^{-6}$ using gamma radiation.

Figure 5:
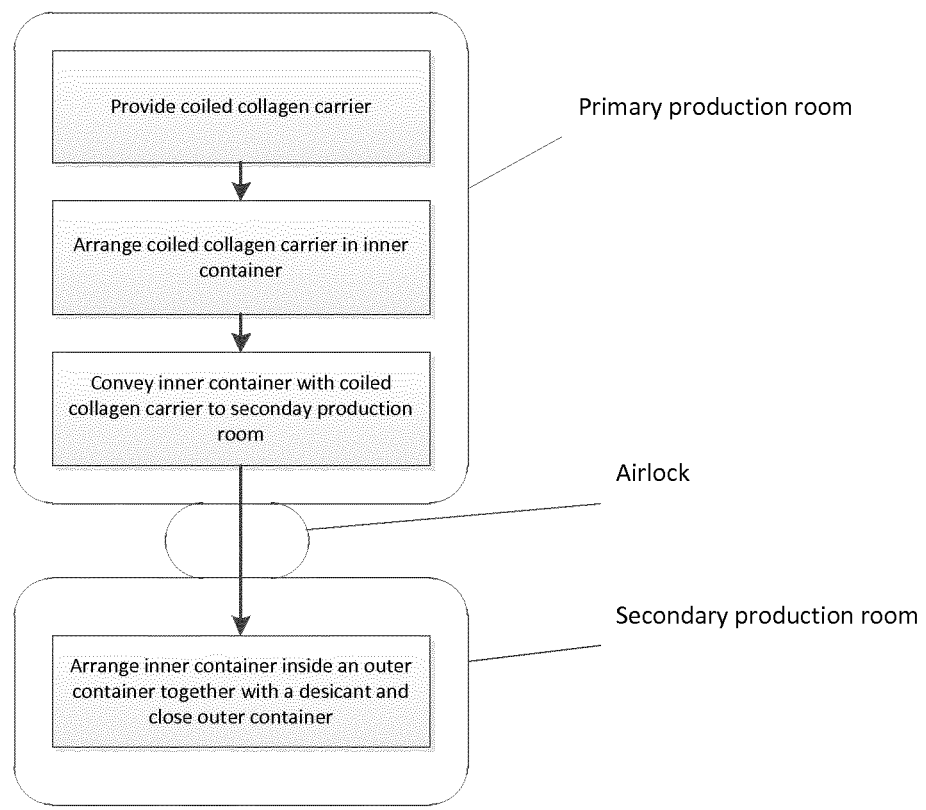

Similarly to what was disclosed in relation to the apparatus according to the invention and with reference to FIG. 5 the process according to the present invention may be divided into a process carried out in a primary production room and a secondary production room. This means that in preferred embodiments, the arranging of the form-stable coiled collagen carrier in the inner container and closing inner container is performed in a primary production room and the arranging of the inner container in an outer container is performed in a secondary production room; the first and the secondary production room be connected with each other by an airlock and the closed inner container is transported from the first to the second room via the airlock.

The process carried out in the secondary production room may further comprise the step of arranging a desiccator inside the outer container prior to sealing of the container and the step of sterilizing the coiled collagen carrier.

A process according to the present invention is typically carried out as an assembly-line process in which the collagen carrier is conveyed without intermediate storing between humidifying and coiling and between coiling and drying.

Furthermore, it is generally preferred that the humidifying of the collagen carrier is performed when a humidified collaged carrier may proceed directly to coiling without any intermediate storing as waiting time for the humidified non-coiled and non-compressed collagen carrier may jeopardise the structural cohesion of the collagen carrier.

Coiled Collagen Carrier

As outlined above, the processes and apparatuses are used to produce form-stable coiled collagen carrier 1. The processes and apparatuses disclosed above have proven to be efficient to produce the coiled collagen carrier 1.

Thus, the present invention provides a coiled collagen carrier 1 having a collagen layer and a coating layer on top of the collagen layer. The coating layer comprising mostly solid thrombin and mostly solid fibrinogen although all the thrombin and/or all the fibrinogen may be solid.

The coiled collagen carrier has typically the shape of an elongated element with a number of windings of the collagen carrier 3 about the longitudinal axis of the elongate element and at least the outer windings and preferably each winding being orientated so that the coating layer constitutes the outer surface of each of the windings. A further characteristic of the coiled collagen carrier 1 is that it is form-stable and defines a collagen carrier in a coiled configuration where at least the outer windings proceed along a spiral in a cross section of the collagen carrier.

The form-stability is often provided by the collagen layer and/or the coating layer has hardened in the coiled shape whereby no additional elements such as constraints are needed to keep the coiled collagen carrier in its coiled shape.

The coiled collagen carrier 1 is in an unrolled configuration a rectangular sheet, preferably having a width, a length and a thickness of the most 4 mm, such as at the most 5 mm, preferably at the most 6 mm, such as at the most 7 mm. The coiled collagen carrier is typically coiled around the width so that the width of the coiled collagen carrier 1 is the width of the unrolled configuration. However coiled collagen carriers being coiled around the length are also an option. A coiled collagen carrier will often comprise three, four or five windings.

A preferred coiled collagen carrier 1 has a cylindrical shape with an outer diameter of less than 12 mm, such as less than 11 mm, such as less than 10 mm, such as less than 9 mm, such as less than 8 mm, such as less than 7 mm, such as less than 6 mm, such as less than 5 mm, such as less than 4 mm, such as less than 3 mm. Furthermore, the coiled collagen carrier has an s-shaped inner most winding about the longitudinal direction of the coiled collagen carrier as disclosed e.g. in FIG. 1.

The coating layer of coiled collagen carriers 1 has no through-going cracks. Often this is obtained by producing the coiled collagen carrier in a manner where the coating layer and/or the collagen layer is(are) softened by humidification prior to coiling which softening allows stretching of the coating layer and/or collagen layer without producing crack or chips (frissures) during coiling. A subsequent drying hardens the softened layer which fixes the coil shape in a form-stable shape. Preferably the coating layer is humidified.

The coiled collagen carrier 1 is often arranged in a container. The container is typically sealed to prevent contamination and/or degradation and/or to maintain form-stability of the coiled collagen carrier. A desiccant, such as silica gel, may be arranged in the container. Such containers with coiled collagen carrier 1 is considered within the scope of the invention In a particular preferred embodiment, a packed coiled collagen carrier 1 comprising an inner container and an outer container is provided. The inner container comprises a compartment having a bottom shaped as a segment of a cylinder, and wherein the curved part of the cylinder segment extends at least 180° as disclosed in FIG. 1 numeral 8. The cavity is sealed by a tear-off, pull-off or breakable foil and the outer container comprising a sealed pouch inside which the sealed inner container is arranged together with a desiccant.

Figure 6:
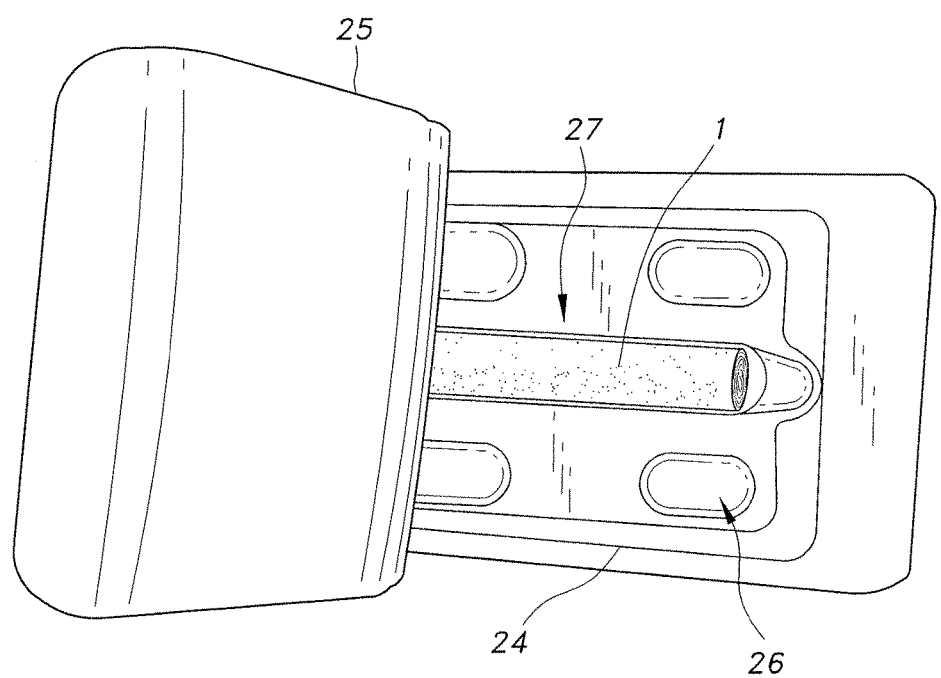
FIG. 6 shows a photograph of a coiled collagen carrier arranged in an inner container with a cover being partly removed.

FIG. 6 shows a photograph of a coiled collagen carrier 1 arranged in a compartment 27 of an inner container 24 with a cover 25 being partly removed. The four cavities 26 are not used for storing any elements but protrude evenly downwardly and provide four legs to enable stable standing on a surface.

Figure 7:
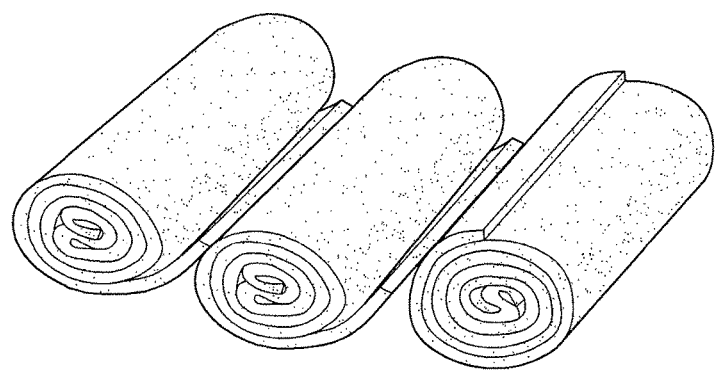
FIG. 7 shows a photograph a three coiled collagen carriers arranged side-by-side on a flat surface.

FIG. 7 shows a photograph a three coiled collagen carriers arranged side-by-side on a flat surface. The coiled collagen carriers shown in FIGS. 6 and 7 are produced according to the invention as disclosed herein.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An apparatus for providing one or more coiled collagen carriers each configured for application to a patient, the apparatus comprising:
   a device for applying moisture to a collagen carrier so as to moisturise the collagen carrier; and
   a coiling device to which the moisturised collagen carrier is conveyed from the moisturising device, the coiling device comprising:
      a pair of elongated members for gripping along an edge of the moisturised collagen carrier and coiling the moisturised collagen carrier in a lengthwise or widthwise direction thereof to produce the coiled collagen carrier; and
      a support device comprising a tray defining a cavity within which said coiling takes place by the rotatable gripping means, said cavity formed by wall segments of the tray against which the moisturised collagen carrier is supported during said coiling, wherein the support device maintains the coiled shape of the moisturised collagen carrier within the apparatus downstream of the coiling device.

2. The apparatus according to claim 1, wherein the pair of elongated members is a pair of tweezers or pincers.

3. The apparatus according to claim 1, wherein the tray cavity is provided with a bottom shaped as a cylindrical segment and with at least one open end, and wherein a curved part of the cylindrical segment extends at least 180°.

4. The apparatus according to claim 3, wherein the cavity is channel-shaped, with the wall segments parallel to one another and extending from the bottom of the cavity.

5. The apparatus according to claim 3,
wherein the elongated members extend into the cavity during said coiling through at least one of the at least one open end.

6. The apparatus according to claim 1, wherein the apparatus is further configured to move the pair of elongated members in reciprocating movement so that the elongated members can be retracted from the collagen carrier after said coiling.

7. The apparatus according to claim 1, further comprising a compressing device selected from the group consisting of a pair of rollers, a pair of even plates, or a rolling object and flat bottom plate, the compressing device configured to compress the moisturised collagen carrier prior to said coiling of the moisturised collagen carrier.

8. The apparatus according to claim 7, wherein the compressing device comprises the pair of rollers.

9. The apparatus according to claim 8, wherein one or both of the rollers are mounted such that the rollers are configured to move apart, said mounting allowing displacement of the one or both rollers in a direction perpendicular to the axis of rotation of the one or both rollers, and wherein the rollers are biased towards each other.

10. The apparatus according to claim 7, further comprising at least one air-conditioning device maintaining the atmosphere surrounding the collagen carrier at a temperature of 18-22° C. and a relative humidity of 30-50% during said moisturising, compressing, and coiling.

11. The apparatus according to claim 7, further comprising at least one drying means selected from the group consisting of a drying tunnel, a pump sucking or blowing air, and a desiccator, the drying means arranged downstream of the coiling device so as to dry the coiled collagen carrier subsequent to said coiling.

12. The apparatus according to claim 1, further comprising at least one drying means selected from the group consisting of a drying tunnel, a pump sucking or blowing air, and a desiccator, the drying means arranged downstream of the coiling device so as to dry the coiled collagen carrier subsequent to said coiling.

13. The apparatus according to claim 12, wherein the drying means comprises the drying tunnel through which the coiled collagen carrier is conveyed while being supported by the support device.

14. The apparatus according to claim 1, further comprising a first conveyer device conveying the collagen carrier downstream of the moisturiser device and towards the coiling device prior to said coiling.

15. The apparatus according to claim 14, further comprising a pair of rollers arranged to compress the moisturised collagen carrier prior to said coiling of the moisturised collagen carrier, wherein the first conveyer device conveys the moisturised collagen carrier to the pair of rollers.

16. The apparatus according to claim 15, wherein the first conveyer device comprises a first conveying element and a second conveying element, the first conveying element conveying the collagen carrier towards the moisturiser device, and the second conveying element conveying the moisturised collagen carrier downstream of the moisturiser device and towards the pair of rollers.

17. The apparatus according to claim 16, wherein more than one of said tray cavity is provided, each of the tray cavities configured to support said coiling of a respective one of said collagen carriers, and said tray being arranged on and conveyed by a second conveyer device of the apparatus.

18. The apparatus according claim 1, further comprising a cabinet sealing at least one of the moisturiser device and the coiling device.

19. The apparatus according to claim 1, further comprising a device for conveying the coiled collagen carrier from the support device and arranging it in an inner container.

20. A production facility in which the apparatus according to claim 1 is arranged in a primary production room of the facility sealed by airlocks.

* * * * *